US011615667B2

(12) United States Patent
Gokcebay et al.

(10) Patent No.: US 11,615,667 B2
(45) Date of Patent: Mar. 28, 2023

(54) LOCKER SYSTEM FOR STORAGE AND DELIVERY OF PACKAGES

(71) Applicant: Digilock Asia Ltd., Lai Chi Kok (HK)

(72) Inventors: Asil Gokcebay, Petaluma, CA (US); Ali Ozhan, Petaluma, CA (US); An Zhang, Shaoguan (CN)

(73) Assignee: Digilock Asia Ltd., Kowloon (HK)

(*) Notice: Subject to any disclaimer, the term of this patent is extended or adjusted under 35 U.S.C. 154(b) by 208 days.

(21) Appl. No.: 16/854,390

(22) Filed: Apr. 21, 2020

(65) Prior Publication Data

US 2020/0349796 A1 Nov. 5, 2020

Related U.S. Application Data

(60) Provisional application No. 62/953,848, filed on Dec. 26, 2019, provisional application No. 62/841,073, filed on Apr. 30, 2019.

(51) Int. Cl.
*G07F 17/12* (2006.01)
*A47G 29/14* (2006.01)
(Continued)

(52) U.S. Cl.
CPC ........... *G07F 17/13* (2020.05); *A47G 29/141* (2013.01); *G07C 9/00896* (2013.01);
(Continued)

(58) Field of Classification Search
CPC .................. A47G 29/141; A47G 29/30; A47G 29/1201; A47G 2029/145;
(Continued)

(56) References Cited

U.S. PATENT DOCUMENTS 1,222,964 A 4/1917 Matchette
1,362,949 A 12/1920 Bibb
(Continued)

FOREIGN PATENT DOCUMENTS

CA 2775847 3/2011
CN 109578857 4/2019
(Continued)

OTHER PUBLICATIONS

EPO machine translation of CN109578857.
EPO translation of disclosure of JP 2002160814.
EPO translation of WO 2008098735.

*Primary Examiner* — William L Miller
(74) *Attorney, Agent, or Firm* — Russell C. Petersen

(57) ABSTRACT

A modular system of locker banks for receipt and delivery of packages is described. The system may include associate modules each having one or more lockers and a control board in communication with each of the lockers in the module. Each locker may include a locker board having a processor and memory configured to control operation of the locker. Each locker may include a lock and a light. The system may further include one or more control modules, each having the above components and further including a kiosk having one or more input and output devices for entering information to the module for controlling operation of the system. The modular system may be connected to a server and/or an administrator terminal.

20 Claims, 20 Drawing Sheets

(51) Int. Cl.
  *G07C 9/00* (2020.01)
  *A61L 2/10* (2006.01)
(52) U.S. Cl.
  CPC .............. *A47G 2029/145* (2013.01); *A47G 2029/149* (2013.01); *A61L 2/10* (2013.01)
(58) Field of Classification Search
  CPC ..... A47G 2029/149; G07F 17/13; A61L 2/10; G06Q 10/0836; E05B 65/0075; E05B 65/025; G07C 9/00912; G07C 9/00944; G07C 9/00896
  USPC ........................................ 232/24, 25, 38, 45
  See application file for complete search history.

(56) References Cited

U.S. PATENT DOCUMENTS

| | | |
|---|---|---|
| 1,574,354 A | 2/1926 | Carl |
| 1,642,533 A | 9/1927 | Beer |
| 1,709,363 A | 4/1929 | Murphy |
| 2,563,094 A | 8/1951 | David |
| 2,658,667 A | 11/1953 | Mirkin |
| 3,784,089 A | 1/1974 | Koch |
| 3,790,244 A | 2/1974 | Stackhouse |
| D248,138 S | 6/1978 | Stackhouse et al. |
| D293,153 S | 12/1987 | McKellar |
| D293,863 S | 1/1988 | Chester |
| 4,836,352 A | 6/1989 | Tateno et al. |
| 4,894,717 A * | 1/1990 | Komei .................. G07F 7/00 348/E7.087 |
| D315,996 S | 4/1991 | Barth et al. |
| 5,172,970 A | 12/1992 | Momose et al. |
| 5,223,829 A * | 6/1993 | Watabe ................ A47G 29/141 340/568.1 |
| 5,231,272 A * | 7/1993 | Mardon ................ G07F 17/13 235/382 |
| D360,738 S | 7/1995 | Schwartz et al. |
| 5,475,378 A * | 12/1995 | Kaarsoo ................ G07F 17/13 235/382 |
| 5,520,450 A | 5/1996 | Colson, Jr. et al. |
| D371,883 S | 7/1996 | Burt et al. |
| 5,774,053 A | 6/1998 | Porter |
| D419,747 S | 1/2000 | Noblet et al. |
| 6,010,064 A * | 1/2000 | Umeda .................. G07F 7/00 235/375 |
| 6,247,641 B1 | 6/2001 | Noblet et al. |
| 6,296,181 B1 | 10/2001 | Noblet et al. |
| D521,155 S | 5/2006 | Shipard |
| D526,065 S | 8/2006 | Shipard |
| 7,748,606 B2 | 7/2010 | Mikolajczyk et al. |
| 9,082,247 B2 * | 7/2015 | Turner .................. G07F 7/00 |
| 9,554,646 B1 * | 1/2017 | Charette ............. B01L 3/50853 |
| D789,022 S | 6/2017 | Spears et al. |
| D795,524 S | 8/2017 | Tartal et al. |
| 9,745,130 B1 | 8/2017 | Rawal |
| D799,783 S | 10/2017 | Spears et al. |
| D799,784 S | 10/2017 | Spears et al. |
| D800,413 S | 10/2017 | Spears et al. |
| D800,414 S | 10/2017 | Spears et al. |
| D802,249 S | 11/2017 | Spears et al. |
| D809,739 S | 2/2018 | Spears et al. |
| D810,389 S | 2/2018 | Spears et al. |
| D811,038 S | 2/2018 | Spears et al. |
| D811,039 S | 2/2018 | Spears et al. |
| D811,688 S | 2/2018 | Spears et al. |
| D859,778 S | 9/2019 | Pieratt et al. |
| 10,439,408 B1 * | 10/2019 | Bastiyali ............ H02J 7/0044 |
| 10,474,797 B2 | 11/2019 | Lowenthal |
| D885,705 S | 5/2020 | Pieratt et al. |
| 10,719,804 B1 | 7/2020 | Lundahl |
| 11,042,142 B2 * | 6/2021 | Xu ......................... H04N 7/18 |
| 11,393,268 B2 * | 7/2022 | Cartwright ............. G07C 9/29 |
| 11,410,118 B2 | 8/2022 | Fee |
| 2001/0017507 A1 * | 8/2001 | Hara .................... A47G 29/141 312/326 |
| 2002/0130172 A1 * | 9/2002 | Hara .................... A47G 29/141 232/18 |
| 2002/0180580 A1 * | 12/2002 | Gotfried ................. G07F 17/13 340/5.2 |
| 2005/0179349 A1 | 8/2005 | Booth et al. |
| 2006/0152339 A1 * | 7/2006 | Mercier ................. G07F 17/13 340/5.73 |
| 2010/0026147 A1 * | 2/2010 | Mackillop ............. E05C 19/002 312/215 |
| 2010/0026452 A1 * | 2/2010 | Wilms .................... G07F 17/12 340/5.73 |
| 2012/0062362 A1 | 3/2012 | Rudduck |
| 2012/0086314 A1 * | 4/2012 | Bourke ................... G07F 17/10 312/109 |
| 2012/0326840 A1 * | 12/2012 | Frankenberg ........... G07F 17/13 340/5.65 |
| 2013/0264381 A1 * | 10/2013 | Kim ....................... G07F 17/13 232/24 |
| 2015/0120601 A1 | 4/2015 | Fee |
| 2015/0179006 A1 | 6/2015 | Von Zurmuehlen et al. |
| 2015/0186840 A1 * | 7/2015 | Torres ..................... A47F 10/02 705/339 |
| 2015/0356801 A1 | 12/2015 | Nitu |
| 2016/0066732 A1 * | 3/2016 | Sarvestani ........... A47G 29/141 232/24 |
| 2017/0061373 A1 * | 3/2017 | Hara ................... G06Q 10/0836 |
| 2017/0116571 A1 | 4/2017 | Tammattabattula |
| 2017/0215620 A1 * | 8/2017 | Dade .................... F25D 17/00 |
| 2017/0278063 A1 * | 9/2017 | Dixon .................. G06K 7/1413 |
| 2017/0286905 A1 * | 10/2017 | Richardson ........ G06Q 10/0832 |
| 2018/0091503 A1 | 3/2018 | Tang |
| 2018/0101820 A1 | 4/2018 | Peynet |
| 2018/0182189 A1 | 6/2018 | Lakshmi-Ratan |
| 2018/0190054 A1 | 7/2018 | Perez |
| 2018/0372447 A1 | 12/2018 | Hyde |
| 2019/0026968 A1 | 1/2019 | Tartal |
| 2019/0051090 A1 | 2/2019 | Goldberg |
| 2019/0114585 A1 * | 4/2019 | Fee .................... G06Q 10/0836 |
| 2019/0313828 A1 * | 10/2019 | Schmider ............... G07C 9/253 |
| 2019/0333304 A1 | 10/2019 | Flynn |
| 2019/0370744 A1 * | 12/2019 | Fee ..................... G06Q 10/087 |
| 2020/0012245 A1 * | 1/2020 | Marin Pulido ...... G06K 7/1417 |
| 2020/0066077 A1 | 2/2020 | Hara |
| 2020/0066086 A1 | 2/2020 | Fee |
| 2020/0187694 A1 * | 6/2020 | Santangeli ......... G07C 9/00571 |
| 2020/0250614 A1 | 8/2020 | Zhu |
| 2020/0293990 A1 * | 9/2020 | Mak .................... G06K 7/10366 |
| 2020/0394857 A1 | 12/2020 | Lin |
| 2020/0408028 A1 | 12/2020 | Schmider |
| 2020/0410797 A1 | 12/2020 | Gomez Santamaria |
| 2021/0000275 A1 * | 1/2021 | Excoffier ............... G06V 20/52 |
| 2021/0235891 A1 | 8/2021 | Derosa |
| 2021/0259449 A1 | 8/2021 | Rosello Ciscar |
| 2021/0293465 A1 * | 9/2021 | Cartwright ........ G06Q 10/0832 |
| 2021/0327185 A1 | 10/2021 | Shelton |
| 2022/0028192 A1 * | 1/2022 | O'Rourke ........... G07C 9/00912 |
| 2022/0051514 A1 | 2/2022 | Schmidt |
| 2022/0068078 A1 | 3/2022 | Schmidt |
| 2022/0084338 A1 | 3/2022 | Mitris |
| 2022/0101258 A1 | 3/2022 | Fujisawa |
| 2022/0170989 A1 | 6/2022 | Froissart |
| 2022/0335758 A1 | 10/2022 | Tazume |

FOREIGN PATENT DOCUMENTS

| | | | |
|---|---|---|---|
| CN | 210072808 U | * | 2/2020 |
| JP | H09201272 A | * | 8/1997 |
| JP | 2002160814 | | 6/2002 |
| WO | 2008098735 | | 8/2008 |

\* cited by examiner

LOCKER SYSTEM FOR STORAGE AND DELIVERY OF PACKAGES

CROSS-REFERENCE TO RELATED APPLICATIONS

This application claims priority to U.S. Provisional Application No. 62/841,073, filed on Apr. 30, 2019, and U.S. Provisional Application No. 62/953,848, filed on Dec. 26, 2019.

FIELD OF THE DISCLOSURE

The present disclosure relates generally to the field of delivery container systems that securely store goods for consumer pick-up. More particularly, a customer can order goods from a retailer, and the system coordinates the storage of these goods in a secure locker. The consumer can retrieve the goods at his or her convenience.

BACKGROUND

Package delivery locker systems can be used by courier services, retail stores, and on-line vendors to aid in facilitating last mile delivery of orders made by recipients, such as through "buy online, pick-up in store." These locker systems are often made up of several lockers, each individually controllable by an adjacent controller and used for securely storing packages of multiple recipients for later pick-up.

DETAILED DESCRIPTION

Reference will now be made in detail to examples of a package delivery system 10, examples of which are disclosed in the associated figures. Wherever possible, the same or corresponding parts will be referred to by the same or similar reference numbers across the drawings. Moreover, when more than one element of the same type is present, reference may be made either collectively or individually. Such reference is only exemplary, and, furthermore, reference to elements in the singular includes the plural and vice versa without limitation to the exact number or type of such elements. Headings used herein are for ease of reference, and no limitation should be read into the disclosure based on the headings.

Figure 1:
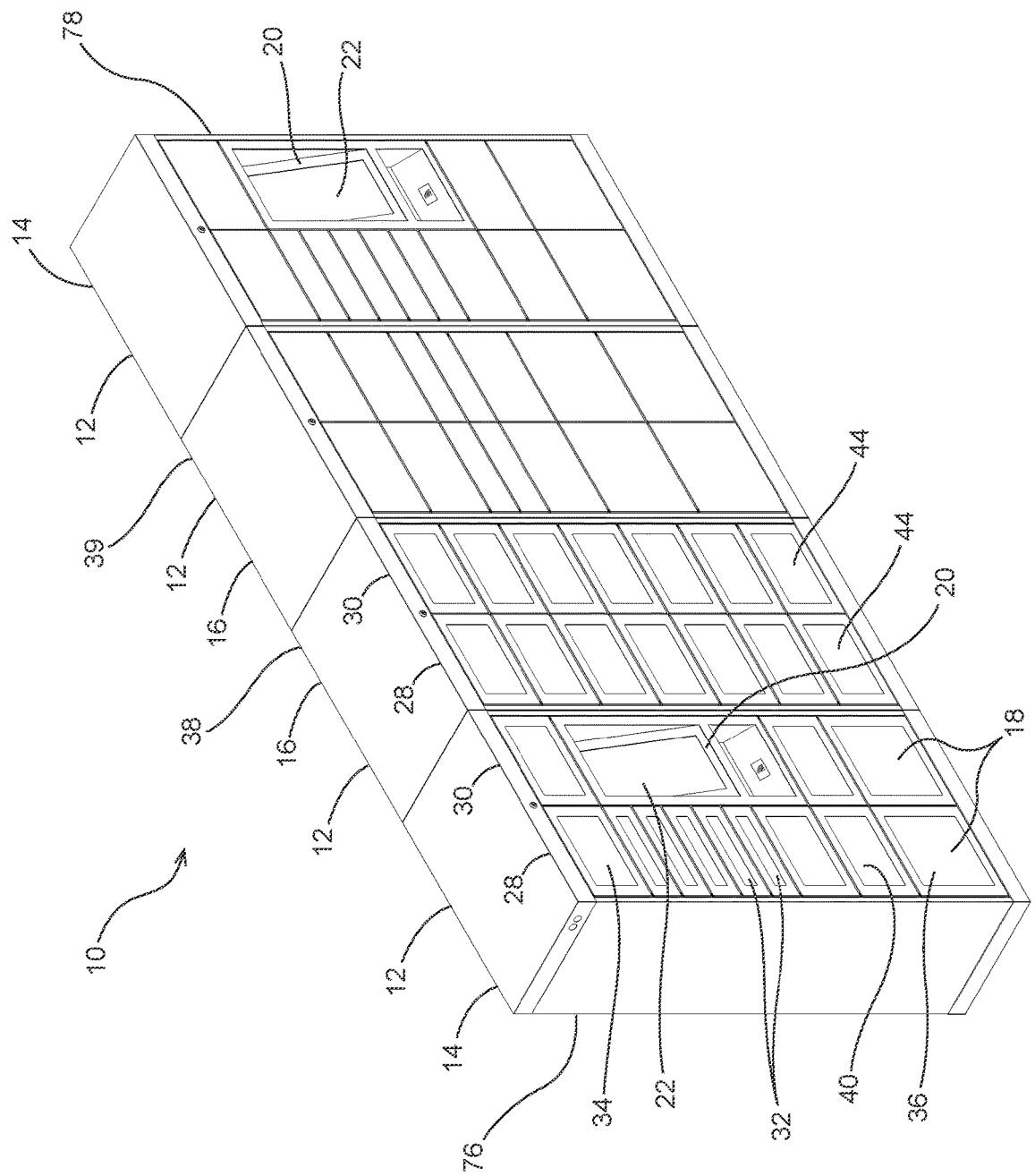
FIG. 1 is a perspective view of a first example of a package delivery system having two control modules and two associate modules.

FIG. 1 discloses an example of the package delivery system 10 that allows for a recipient to securely receive items that they have ordered. Although the system 10 is described in one example herein as a package delivery system that can be used by a courier, the system 10 can be employed in other applications in addition to securing packages for delivery. For example, retailers can also use the package delivery system 10 for securing products ordered by their on-line customers for pick-up. A large condominium building or dormitory could employ it as a secure method of delivering documents or other materials to their owners and/or tenants or as a secure location for drop-off of packages by a courier ordered by the tenants or owners that are too large to fit in their mailboxes. The disclosed exemplary system 10 advantageously creates a record of both delivery of the item to the system 10 and a record of the recipient retrieving the item from the system 10. In other useful examples, the system 10 can used in the service and repair industry, such as in a laundromat or dry-cleaning business, where clothing that has been cleaned can be stored in the lockers awaiting pick-up. Similar uses include securely storing items for pick-up that have been repaired, such as personal computers, shoes, watches, and the like. The system 10 can also be refrigerated and store groceries, either for in-store pick-up or for delivery drop-off at a predetermined location. Moreover, the system 10 could be heated and store prepared food while awaiting consumer pick-up.

In another non-limiting example of use, the delivery system 10 can also be used as a drop-off location for consumers, such as for returning unwanted products or to ship goods to others. The delivery system 10 could further include a printer capable of printing delivery labels that can be applied to the packages to be returned or shipped. The user would also have the option of printing delivery labels via their home computer. The courier can retrieve the package from the locker and return it to the manufacturer or send it to whatever destination indicated by the user. Similarly, the consumer can drop off clothing to be laundered or a product to be repaired, and the service provider can retrieve the product and perform the required service.

Figure 2:
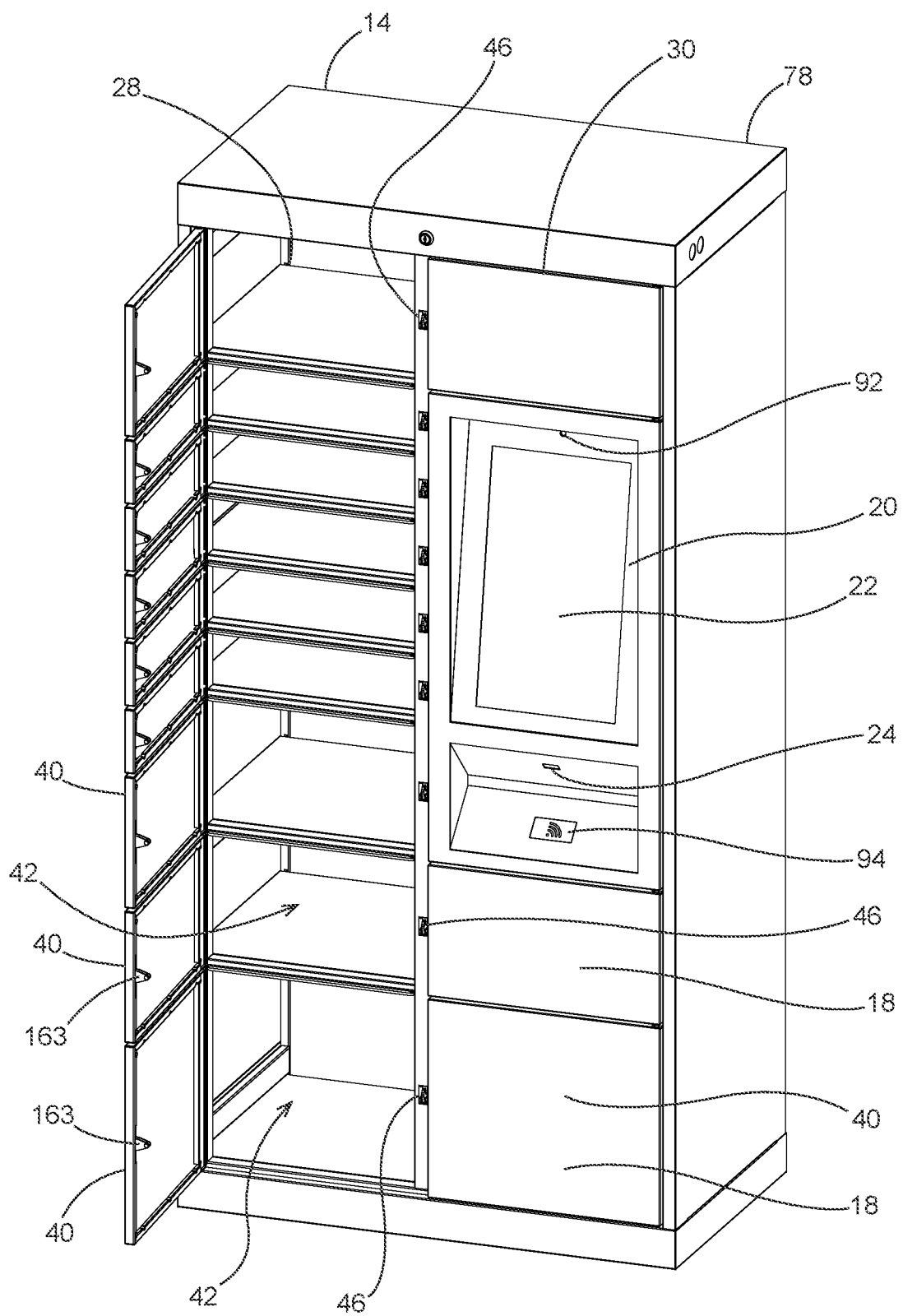
FIG. 2 is a perspective view of a control module of the package delivery system of FIG. 1 with a plurality of locker doors in a fully open position.

Referring now to FIGS. 1 and 2, the package delivery system 10 includes a series of modules 12 including two control modules 14 and two associate modules 16. Both the control modules 14 and the associate modules 16 include a plurality of lockers 18 that can be arranged in any needed configuration and have a plurality of sizes. Each of the control modules 14 includes a kiosk 20 designed to allow, for example, couriers, retail employees, and recipients to input information to the package delivery system 10 to gain access to the lockers 18 and to store and retrieve items contained within the lockers 18. As will be described below, each kiosk 20 can control each and every locker 18 within the package delivery system 10, and the kiosks 20 can also receive information from each of the lockers 18 as well. Although two control modules 14 and two associate modules 16 are depicted, more or fewer modules 14, 16 can be used, according to the needs of the end users.

The kiosks 20 are disposed in the control modules 14 and include data output devices including a display 22 and/or a speaker (not shown) for providing information to the user. The speaker is particularly useful for the visually-impaired. The kiosks 20 also include data input devices for receiving information, such as authentication information, from the user. The display 22 can also a touchscreen and therefore can function as a data input device as well. Other data input devices can include a barcode reader 24, a digital camera 92, a mobile ID reader 94, or other input devices, including RFID readers, keyboards, track balls, mouses, microphones, biometric identification devices, or USB ports. As is known, the mobile ID reader can include NFC, Bluetooth, BLE, or other mobile technologies. Other known data input devices are well-known in the art. The package delivery system 10 can use these input devices in variety of ways to collect the needed information from a user and from packages and can use this information when making decisions.

The control modules 14 can have a standard configuration that includes the kiosk 20 and a predetermined layout of lockers 18. The configuration of FIG. 1 discloses a first control module 76 and a second control module 78. The control modules 14 include lockers 18 configured in a left column 28 and a right column 30 with small lockers 32, medium-sized lockers 34, and large lockers 36 at the bottom as shown. The associate modules 16 can have different configurations with different layouts of lockers 18 and no kiosk 20. The first associate module 38 includes left and right columns 28, 30 of medium sized lockers 34. The second associate module 39 includes left and right columns 28, 30 of lockers 18, with small lockers 32, medium-sized lockers 34, and large lockers 36 at the bottom. Other configurations for both the control modules 14 and associate modules 16 are, of course, possible.

The lockers 18 of both modules 14, 16 of the system 10 are suitable for receiving and storing packages, letters, and other items that likewise will have various dimensions. Obviously, different dimensions and more or fewer categories of locker sizes can be employed. In fact, as associate module 16 may include a single locker 18 that is very large. The lockers 18 can be made of durable materials such as high-strength steel to protect against unauthorized entry.

Referring now to FIG. 2, each locker 18 includes a door 40 that selectively provides access to a locker interior 42. Each locker door 40 is hingedly attached to its respective locker 18. In this embodiment, the door 40 is hinged on one side and opens outwardly to allow access to the locker interior 42 such that the interior 42 can be accessed and items can be deposited and retrieved from inside the locker 18. Each door 40 is selectively closeable by closing the door 40 such that the door's associated strike 163 is inserted into the door's lock 46, as will be discussed in detail below. Each door 40 is mounted to each locker 18 by a high-strength hinge and can be spring-biased outwardly such that when the locker door 40 is in a closed position and the lock 46 is unlocked, the door 40 will swing open automatically and allow access to the interior 42 of the locker 18. In another embodiment, the locker door 40 itself is not biased towards an open position. Instead, when the lock 46 unlocks, the lock 46 generates a force to automatically push the door 40 open. Of course, a door 40 could be both spring-biased and receive an opening force from the lock 46.

In one example, the locker door 40 can be the same material as the locker itself, e.g. high-strength steel. In another example, the locker door 40 can include a window 44 (best seen in FIG. 2A) that allows a user to view the contents of the interior of the locker. Such window 44 can be made of phenolic resin, polycarbonate, or another impact-resistant, transparent sheet. In the examples depicted in FIGS. 1 and 2, the first control module 76 and the first associate module 38 include locker doors 40 with windows 44. The second associate module 39 and the second control module 78 include locker doors 40 of the same material of the locker itself. Of course, the locker door can be a different material for various reasons, including cost and/or aesthetics.

Figure 2A:
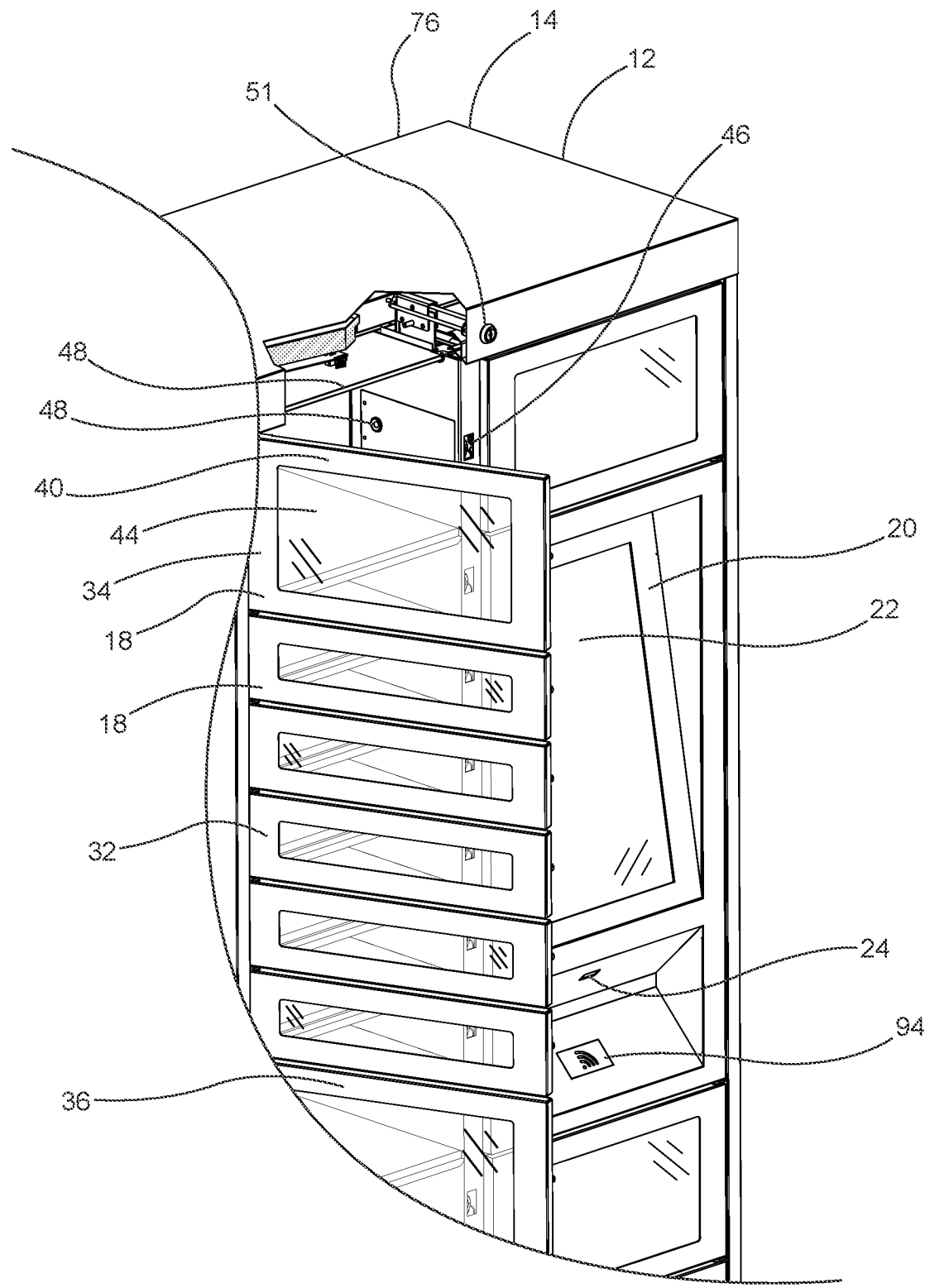
FIG. 2A is a detail perspective view of a control module of the package delivery system of FIG. 1, in partial cut-away and with several locker doors in a fully open position, in particular showing the lock and lighting of a locker.

As best seen in FIGS. 2 and 2A, each locker 18 further includes an electronically-operated latch-type lock 46 that selectively locks its respective door 40 in the closed position. The lock 46 secures the door so that the items within the locker 18 are only accessible to authorized users. The disclosed system 10 is not limited to latch-type locks 46, and other locks known in the art can be used to selectively secure the doors 40 in a closed position.

Disposed within each locker interior 42 is an illumination source 48 such as an LED light 48 that is configured to illuminate the locker interior 42. In one example, the LED light 48 is in communication with the lock 46 itself such that the lock 46 can coordinate the lighting of the LED light 48. The LED light 48 can be configured such that it is illuminated whenever a locker door 40 is opened. Further, the system 10 can be configured such that the LED light 48 stays illuminated when a package or other item is disposed within the associated locker 18, even when the locker door 40 is closed. This can be especially useful when the locker door 40 includes a window 44 so as to draw attention to and highlight the lockers 18 that have packages or other items disposed therein and are awaiting pickup.

As shown in FIG. 2A, the LED light 48 can be disposed near the lock 46 on a side panel of the locker 18. Also as shown in FIG. 2A, the LED light can be a linear light mounted to or near a ceiling panel of the locker 18. While both LED lights are shown in FIG. 2A, it is possible that one or the other of the disclosed LED lights 48 are employed. Therefore, the LED light 48 is not necessarily disposed on the lock 46 itself, and it can be connected via wiring to the lock 46 to allow placement of the LED light 48 within the locker 18. Further, the LED light 48 can have a rope light configuration to provide different illumination effects. With a rope light configuration, the LED light 48 could be disposed on the ceiling of the locker 18 or around the circumference of the window 44. Moreover, the lock 46 can be configured to illuminate or flash the LED light 48, or the lock 46 can illuminate the LED light 48 in different colors and different times or under different circumstances, such as seconds prior to the locker door 40 opening to draw attention to the locker 18 prior to its opening. More than one LED light 48 can be used, and other lighting sources, such as compact fluorescent bulbs, could be used as well.

In one example, each lock 46 is activated and locks the locker door 40 when the door 40 is shut; and when the proper credentials are input and the lock 46 is unlocked, the locker door 40, which is biased to be opened, opens automatically.

The interior 42 of the lockers 18 can further include several sensors. For example, the latches contained within the locks 46 include sensors regarding whether they are in the locked or unlocked state. Further, the locks 46 may be connected to proximity sensors that are configured to sense whether the locker door 40 is open or closed. The lock 46 can further be connected to a temperature sensor to record the temperature of the interior of the associated locker. Other sensors, such as weight sensors and optical sensors, can be employed to confirm the presence or absence of a package or item within the locker interior 42. Finally, as depicted in FIG. 2A, the modules 12 include a mechanical override lock 51, such that operation of the mechanical override lock 51 can open all doors 18 at once. The mechanical override lock 51 can be connected via a one or more and connectors and/or levers (not shown) to each lock 46.

Figure 2C:
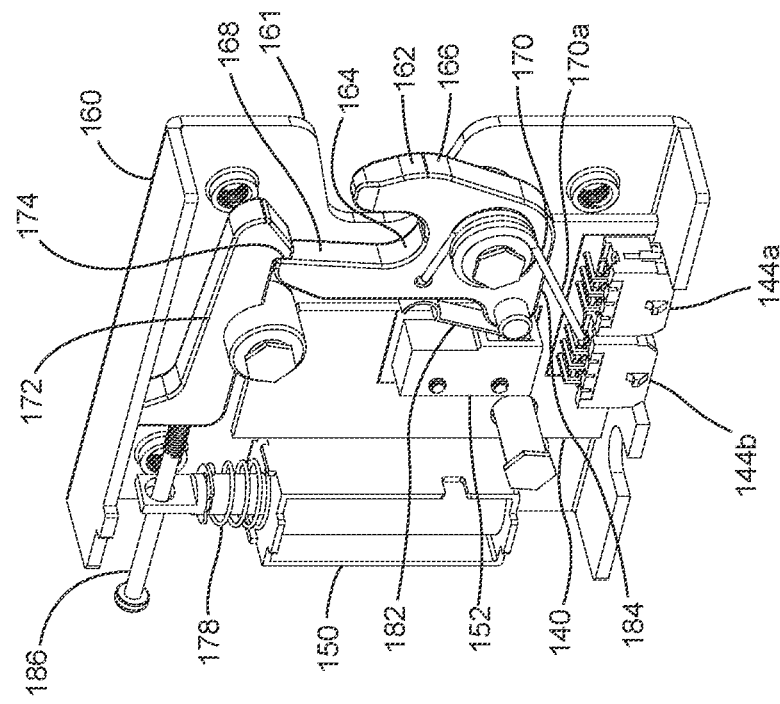
FIG. 2C is a perspective view of the lock of FIG. 2B.
Figure 2B:
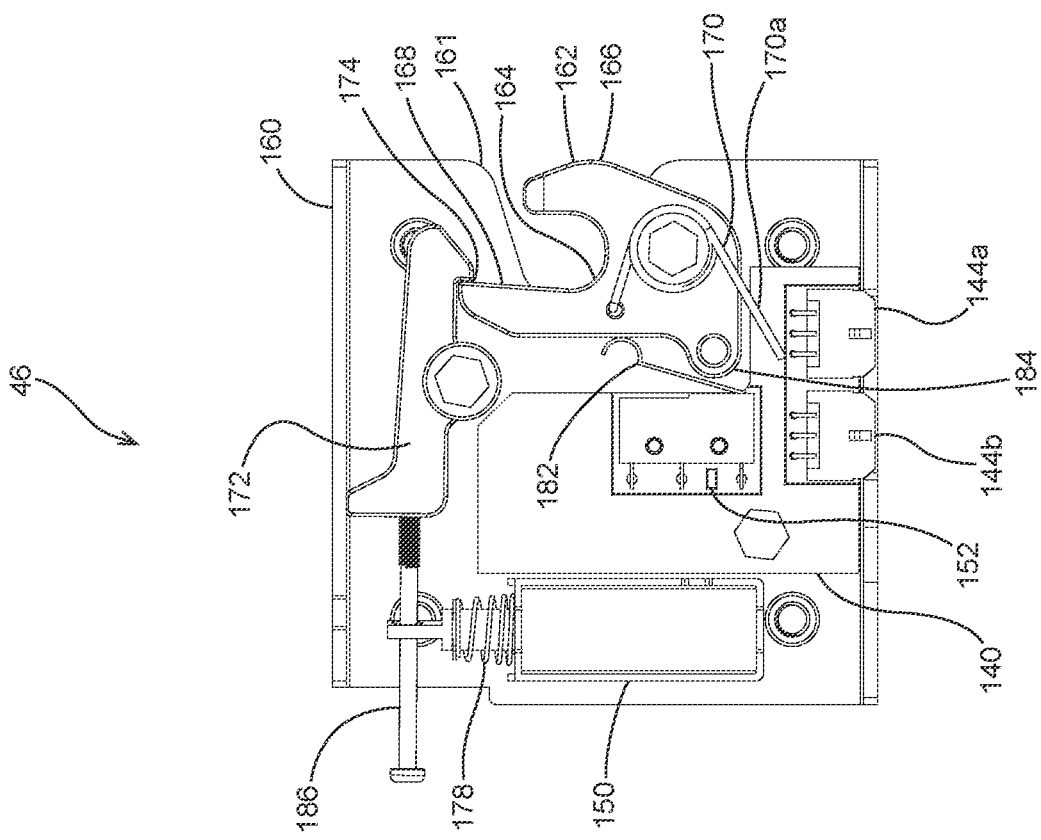
FIG. 2B is a plan view of a representative lock in a locked position, with a portion of the housing removed for clarity, useful with the lockers of the package delivery system of FIG. 1.
Figure 2E:
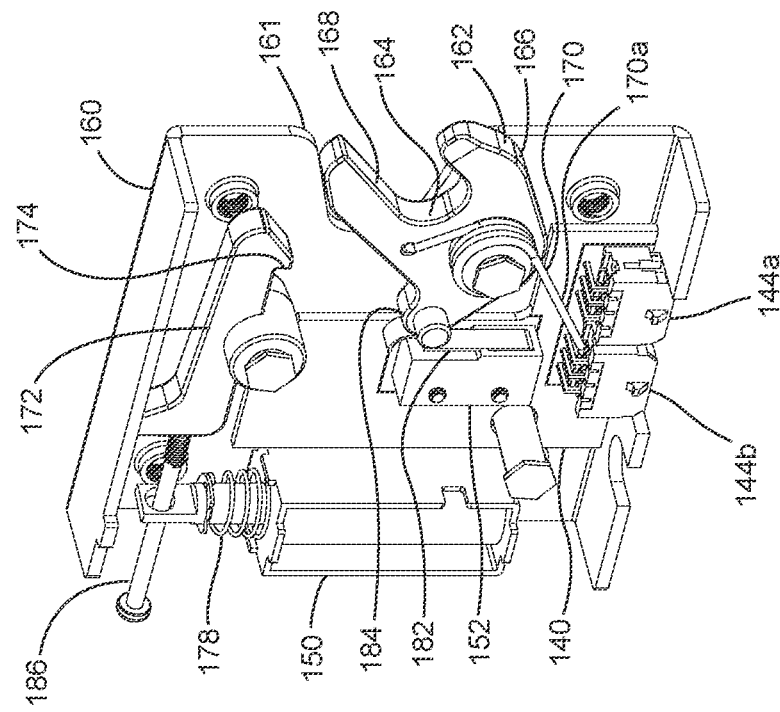
FIG. 2E is a perspective view of the lock of FIG. 2D.
Figure 2D:
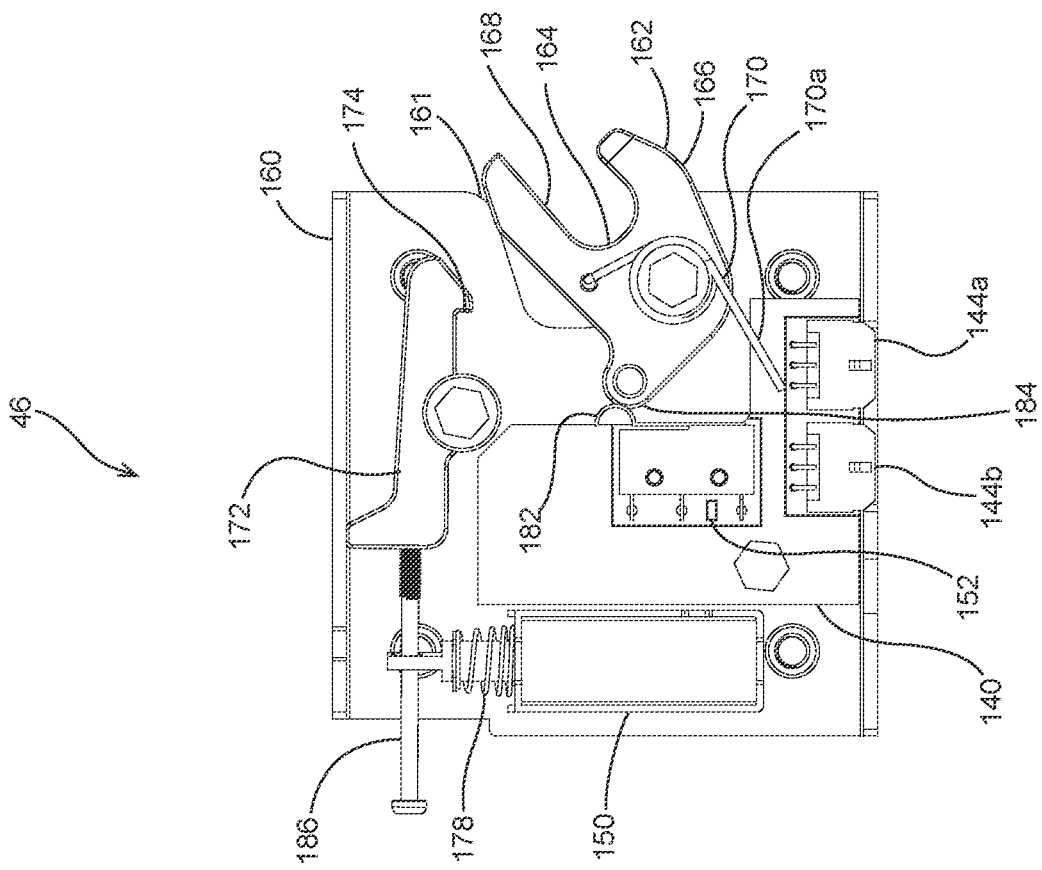
FIG. 2D is a plan view of the lock of FIG. 2B in an unlocked position.

Referring now to FIGS. 2B and 2C, an example of the internal mechanics of the lock 46 is shown. The lock 46 includes a housing 160 having a recess 161 providing access to a latch hook 162. The latch hook 162 is pivotable and includes a latch hook recess 164 sized and shaped to receive a strike 163 (shown in FIG. 2) associated with the locker 18, as is known in the art. The latch hook 162 has a first leg 166 and a second leg 168 that is longer than the first leg 166. The latch hook 162 is rotatable between a first locked position, as shown in FIGS. 2B and 2C, wherein the latch hook 162 can retain the strike 163 within its recess 164, and an unlocked position shown in FIGS. 2D and 2E, where the latch hook 162 has rotated in a clockwise direction and released the strike 163.

The latch hook 162 is biased in the housing 160 in a clockwise direction by a torsion spring 170 to the unlocked position. As will be understood, the housing 160 includes a portion not shown in FIGS. 2B-2E, i.e. the portion that has been removed to allow the mechanics to be visible. The torsion spring 170 includes an end 170a that is affixed to that portion of the housing 160 that has been removed in the figures. Accordingly, the end 170a of the torsion spring 170 remains fixed to the same location while the latch hook 162 rotates, which allows the torsion spring 170 to compress and provide the biasing force. As discussed previously, the force generated by the torsion spring 170 when the lock 46 switches from the locked position to the unlocked position can be great enough to throw the locker door 40 open.

A latch 172 is further disposed in the housing 160 and is pivotable. The latch 172 includes a lip 174 that engages the second leg 168 of the latch hook 162 to maintain the latch hook 162 in the locked position against the biasing force of the torsion spring 170. When the latch 172 pivots in the counter-clockwise direction, the latch lip 174 releases the second leg 168, and the latch hook 162 rotates from the locked position to the unlocked position under the force of the torsion spring 160.

A linear actuator 150 controls, in part, the rotation of the latch 162, and is biased by a coil spring 178 outwardly to bias the latch 172 to the position shown in FIGS. 2B and 2C. When the actuator 150 is actuated, the actuator 150 pulls the latch 172 downwardly, which thereby releases the latch 172 from the latch hook 162, allowing the latch hook 162 to rotate under the force of the torsion spring 170, and thereby automatically opening the locker door 40. The actuator 150 can be any electrically operated actuator known in the art, including, for example, a solenoid or an electric motor.

The actuator 150 is connected to lock circuit board (or, simply, lock board) 140 that contains a microprocessor 142 (shown in FIG. 7) with associated logic to determine if the system 10 should unlock the lock 46, and thereby open the locker door 40. Disposed on the lock board 140 is a first connector 144a that receives power and control signals regarding the lock status. The lock board 140 further includes a second connector 144b that passes on power and control signals to the other locks 46 in the module 12. Finally, a mechanical limit switch 152 is disposed on the lock board 140 and includes a lever 182. The latch hook 162 further includes a lobe 184 that can selectively engage the lever 182 of the limit switch 152 to provide feedback regarding the latch hook's 162 position. In the locked position, the lobe 184 does not engage the lever 182, but when the latch hook 162 is rotated to the unlocked position, the lobe 184 bears on the lever 182 and triggers the switch, thereby providing feedback that the lock 46 is unlocked.

The lock 46 is further manually operable by way of a lever 186 extending out the back of the latch 172 and outside of the housing 160. Accordingly, if a user wishes to manually unlock the lock 46, he or she need only push the lever 186 downwardly (as shown in FIG. 2B) and the latch 172 will disengage the latch hook 152, thereby allowing the lock 46 to shift to the unlocked position as described above. As discussed above, by operating the override lock 51, the attached levers and connectors can mechanically push on the levers 186 of each lock 46 generally simultaneously, thereby shifting all locks 46 in the system 10 to the unlocked position.

Figure 3:
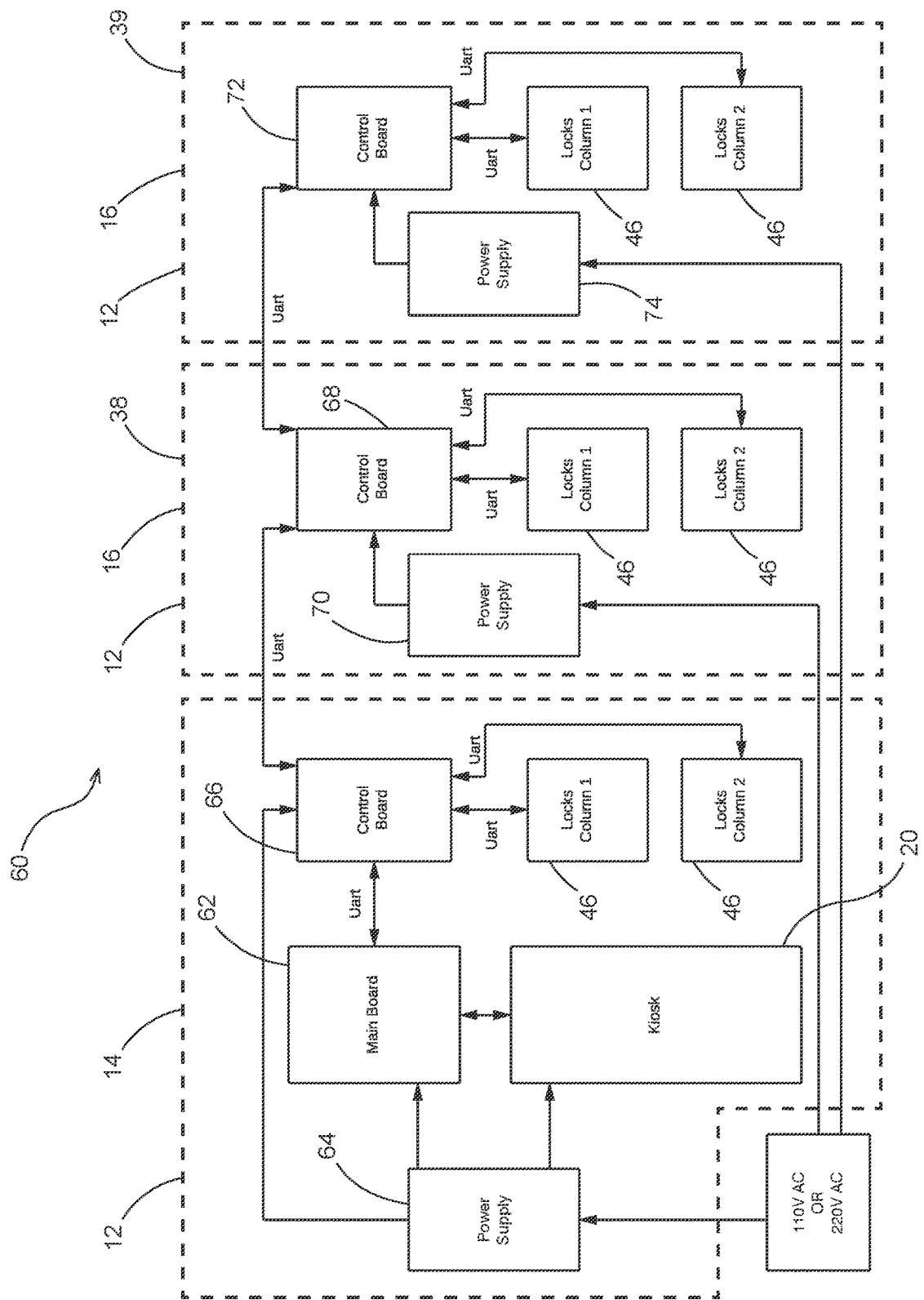
FIG. 3 is a schematic depicting the main electronic components of the package delivery system of FIG. 1 and their connections.

Referring now to FIG. 3, a schematic of the control system 60 for the modules 12 is depicted. The control module 14 includes a kiosk 20 as described above which is connected to a main circuit board 62, and each output device and input device of the kiosk 20 is operatively connected to the main board 62. The main board 62 receives power from a power supply 64. The main board 62 of the control module 14 is connected to a control board 66 within the module 14 via a UART connection. The control board 66 is connected to each and every lock 46 within the control module 14, again via UART connections.

The control board 66 of the control module 14 is also connected via UART connection to a control board 68 housed in the first associate module 38. The control board 68 of the first associate module 38 is likewise powered by a power supply 70. The control board 68 is connected via UART to each and every lock 46 within the first associate module 38. Finally, the control board 68 of the first associate module 38 can be connected to a control board 72 in the second associate module 39. The control board 72 in the second associate module 39 also is powered by a power supply 74 and is connected via a UART connection to each of the locks 46 in the second associate module 39.

As will be understood, the control board 72 of the second associate module 39 can be connected to a control board in the second control module 78, and, as described above, the second control module 78 can be constructed substantially the same as the first control module 76. In this manner, the kiosks 20 of both the first control module 76 and the second control module 78 are connected to and in communication with each and every lock 46 in the package delivery system 10. Multiple control modules 14 can be advantageous to allow for multiple users of the package delivery system 10 at one time. In other words, two people may simultaneously be retrieving their items from the lockers 18 within the package delivery system 10. As can be seen in FIG. 3, each control board 66, 68, 72 has separate connections for locks 46 in the left column 28 and for the locks 46 in the right column 30. Further, the system 10 is effectively modular in that one or more control modules 14 can be employed, and any number of associate modules 16 can be employed, depending on the floor size available and the number of lockers 18 needed, and they can easily be connected and disconnected.

Figure 4:
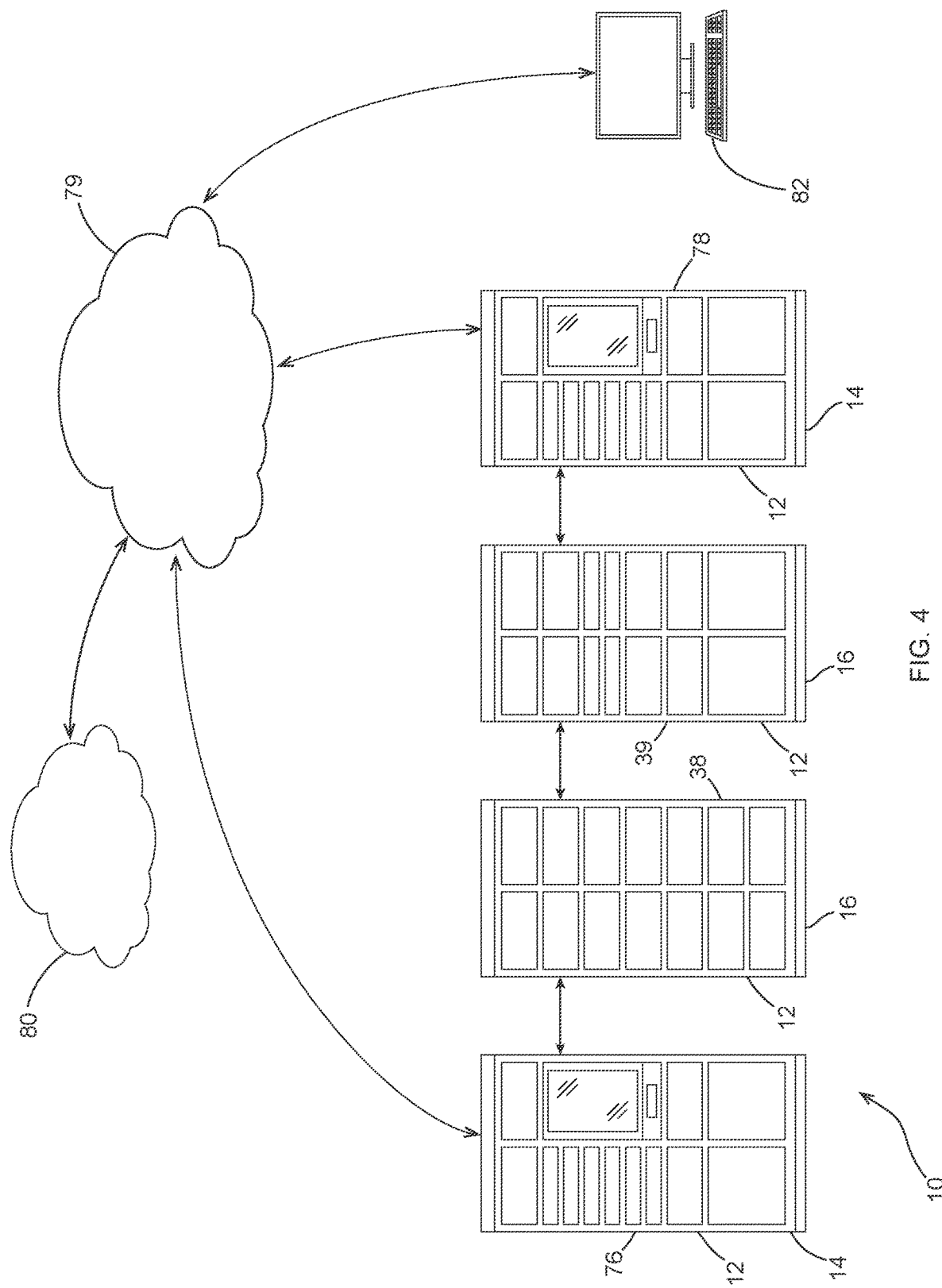
FIG. 4 is a schematic depicting components of the control modules and a cloud-based server.

Referring now to FIG. 4, the main boards 62 of the control modules 14 may include a Wi-Fi or WLAN chip and antenna, or other wired or wireless transmitter for connecting the system 10 to a router and a network 79, such as, for example, one or more of the Internet, a WAN, or a LAN. The control modules 14 can be in communication with a cloud-based server 80 via the Internet that can both monitor and record the operations of the package delivery system 10. Although a cloud-based server is depicted and referred to herein, any server 80 can be used, including local, remote, or other form of dedicated or non-dedicated server. Accordingly, any reference to a cloud-based server shall be understood broadly to encompass any computing device capable of performing the functions described herein.

Further, an administrator may communicate with and control the system 10 remotely using a personal computer device 82 such as a PC, tablet, smart phone, or the like, that is also connected to the network 79 and the server 80. By connecting to the system 10 via a personal computer 82, for example, an administrator may grant, amend, or revoke authorization privileges to users. The administrator may update the locks 46 with the most up-to-date firmware and security protocols and may operate the locks 46 remotely. Further, the system 10 is able to provide reporting and notifications to the administrator such as, for example, audit logs for lock history and user history, current statuses of each display case 18, invalid access attempts, malfunctioning any low batteries, internet outages, the amount of time a package has been stored in a locker 18, and the like. Although a WLAN chip is discussed herein, as discussed above the package delivery system 10 can also be hardwired to the network 79, using known systems and methods or connected to the Internet using any other known method.

The main boards 62 can further communicate the ongoing status of the system to the server 80, which can pass the information onto the administrator at the personal computing device 82. For example, the main boards 62 can signal the server 80 that an item has been placed in a locker 18 or retrieved from a locker 18, and the server 80 can serve as a back-up data storage unit. Moreover, for multi-control module systems, the server 80 can pass on information to the control modules 14 that weren't used to execute the transaction to ensure that all control modules 14 have the most up-to-date information. For example, if a user uses the first control module 76 to deposit an item into a particular locker 18, then that locker 18 will not be available until that item is removed. It is important that the second control module 78 be informed of the status of the locker 18 so that it does not assign another drop-off for that locker 18. In this scenario, the first control module 76 signals the server 80 of the drop-off, and the server 80 signals the second control module 78 of the drop-off. The second control module 78 can then update its database to record the unavailability of the locker 18. In another example, the first control module 76 can signal the second control module 78 through the control boards 66, 68, 72.

The cloud-based server 80 can further be configured to communicate with the package recipient. When a drop-off has occurred, the cloud-based server 80 can provide an indication to the recipient that the item is ready for pick-up. Such indication can be via email, text message, or other communication.

In other scenarios, the WLAN chip can be connected to a retailer's IT system. In this case, the delivery system 10 can be configured to notify the retailer upon an item being placed in a locker 18, but the package delivery system 10 will not inform the recipient that the item is ready. Instead, the retailer will inform the recipient that the item is ready, and the delivery system 10 will never be in possession of any information able to identify the recipient. Such configuration can be helpful to minimize the number of systems having access to personally identifiable information.

Figure 5:
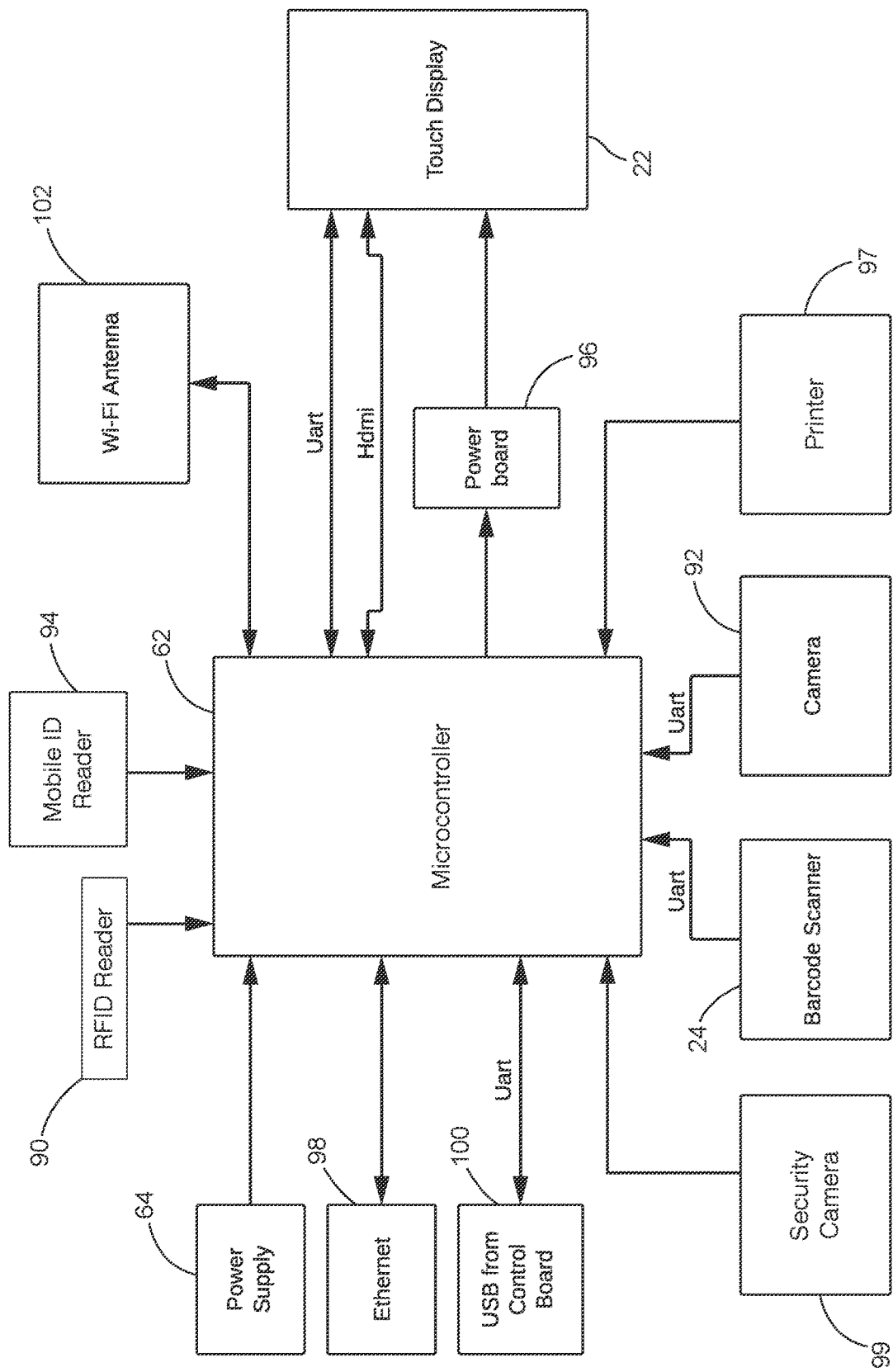
FIG. 5 is a schematic of a main board of the control module.

Referring now to FIG. 5, the main board 62 is detailed. The main board 62 can include one or more processors and memory and is configured to receive the input from the input devices of the kiosk 20. The processors can be configured with logic to render decisions based on the data input by the users via the input devices.

In this example, the input devices are the barcode reader 24, a digital camera 92, and the touchscreen display 22, all connected to the main board 62 via UART. The display 22 also is connected via HDMI to transfer the digital image signals, as well as an independent power supply 96. The main board 62 can further include an Ethernet connection 98 to provide, for example, a hardwired connection to the Internet, a USB connection 100 to connect with its respective control board 66 via UART protocol, and a Wi-Fi dual-band antenna 102 connected to the Wi-Fi chip discussed above for wireless connection to the Internet. Further, the main board 62 can include an RFID reader 90 and/or a mobile ID reader 94 such as NFC, Bluetooth, or BLE. A courier or recipient can input his or her credentials or authorization in this manner. The touchscreen display 22 can further be used to provide further validation of the recipient by requiring a signature before opening of the locker door 40. The recipient may be required to scribe his or her signature on the touchscreen 22 by finger.

The main board 62 can also have a printer 97 connected thereto. The printer 97 can be used in conjunction with a process of printing a shipping label. A user may wish to ship a package to another address. The shipping company can have an application based in the main board 62 that walks the user through the process of creating a shipping label.

Once the shipping label is created, user can affix it to a package, and deposit that package in a locker 18. The package delivery system 10 can notify the shipping company that a package is awaiting delivery, and the shipping company can then retrieve the package and commence the shipping of the package. Such process can simplify and streamline the shipping process.

A security camera 99 may further be in communication with the main board 62 to monitor the package delivery system 10. The output of the security camera 99 may be fed by the main board 62 to the server 80 on an on-going basis, with deletion after a pre-determined amount of time such as two weeks.

Figure 6:
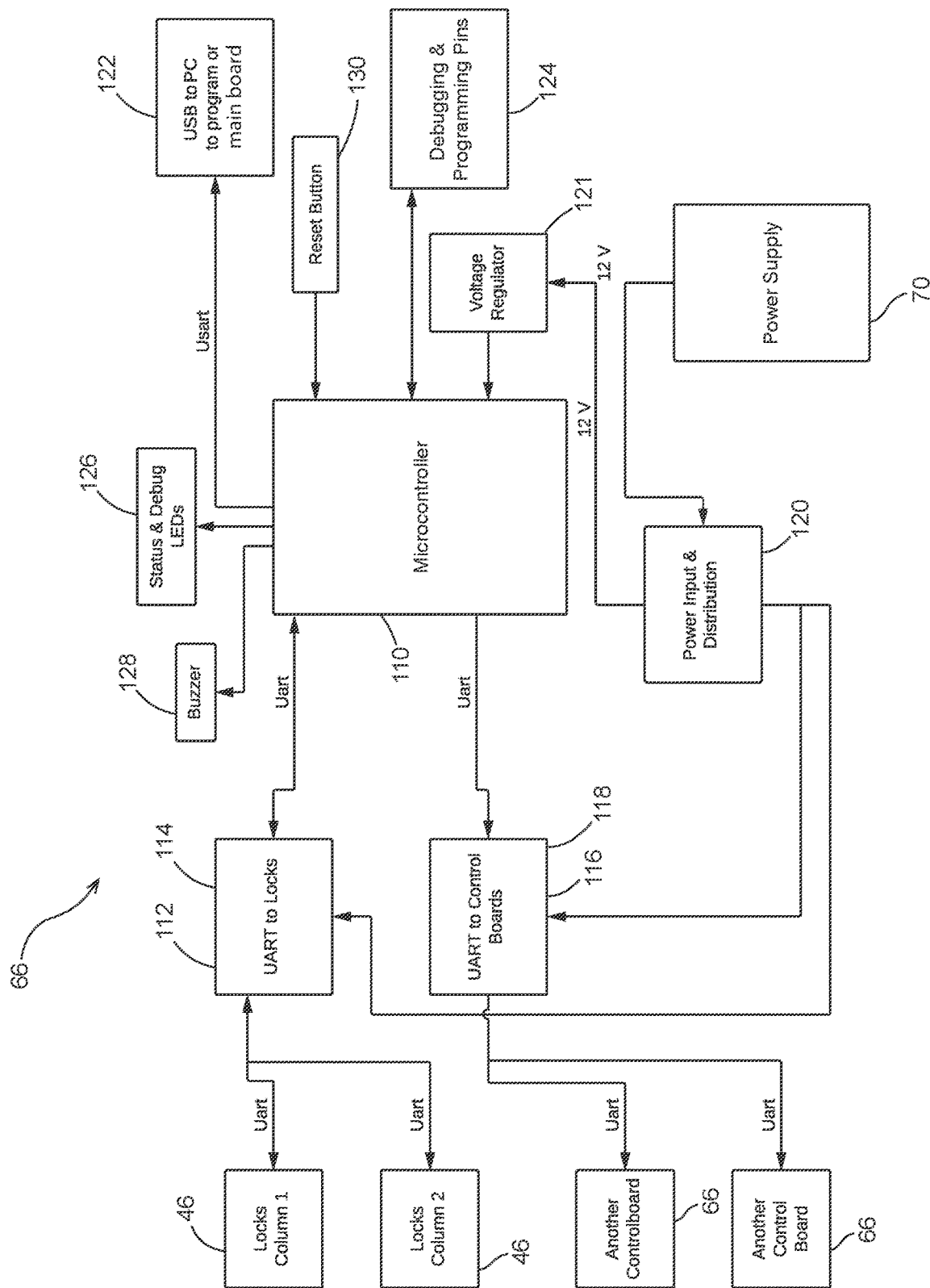
FIG. 6 is a schematic of a control board of the control modules and the associate modules.

Referring now to FIG. 6, each module 12 includes a control board 66 that is substantively the same and is either directly or indirectly in communication with the main boards 62 of the control modules 76, 78. Moreover, the control boards 66 are in communication with each of the locks 46 and can direct the functionality of each of the locks 46 in their respective module 12. In this example, the control board 66 includes a microprocessor 110 having one or more processors and memory. Although control board 66 is described herein, control boards 68, 72 are similar. Further, although the term microprocessor is used herein, it will be understood by one of ordinary skill that any number of structures can be used to effectuate the functions described herein, e.g. controllers, processors, microcontrollers, and addressable switches, and therefore the term microprocessor as used herein shall be understood to be exemplary and encompass all such structures.

The control board 66 includes first and second ports 112, 114, each port serving as a UART connection to a respective column of locks 18. The control board 60 further includes third and fourth ports 116, 118, each of these ports 116, 118 serving as UART connections to control boards 66 of adjacent control modules 14 or associate modules 16. The control board 66 further includes a power input and distribution port 120 that receives power from the power supply 70 and distributes power to the first through fourth ports 112, 114, 116, 118 as well as a voltage regulator 121 that passes on power to the microprocessor 110. The control board 66 further includes a USB connector 122 that, if used in a control module 14, can be used to connect to the main board 62. The USB port 122 can also be used to connect to a PC for programming of the microprocessor 110. The control board 66 can contain several other input and output devices that aid in programming an operating, including an in-circuit programmer/debugger port 124, status and debug LEDs 126, a buzzer 128, and a reset button 130.

Figure 7:
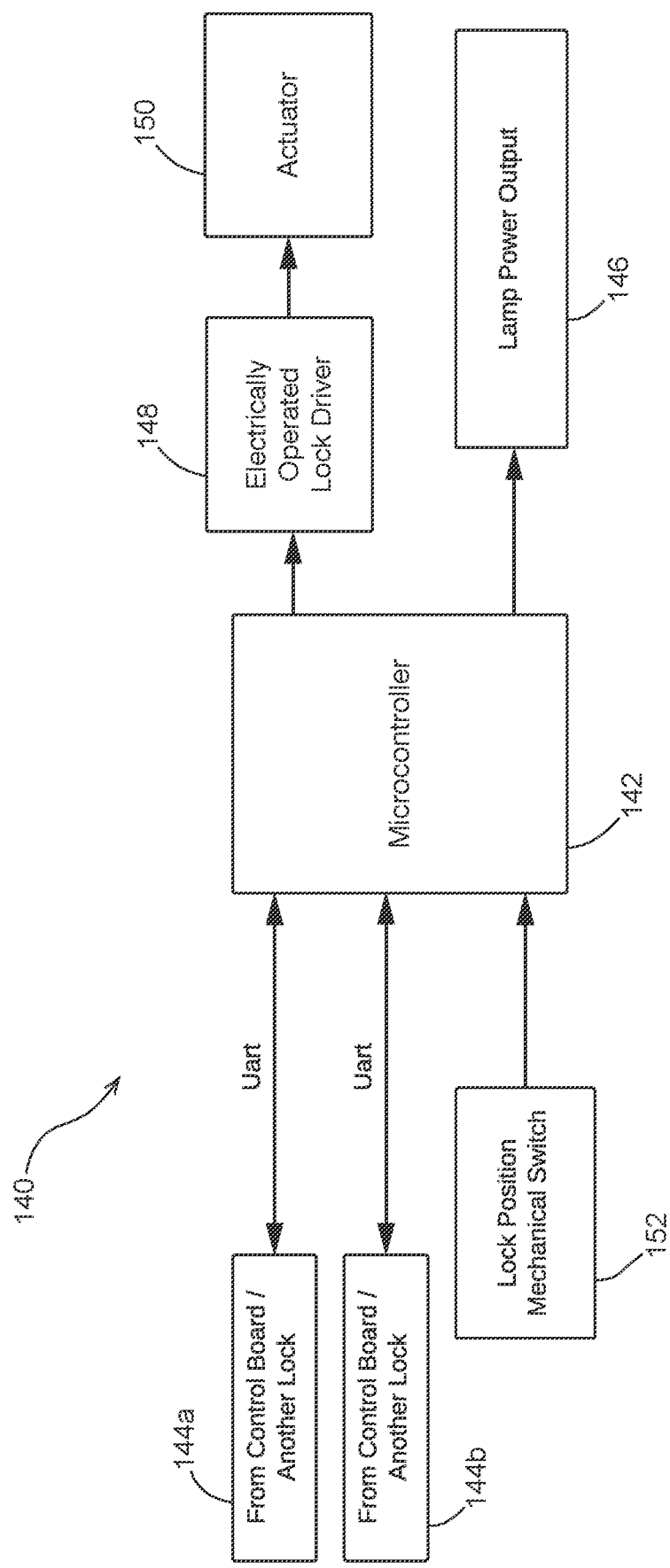
FIG. 7 is a schematic of a lock board of the control modules and the associate modules.

Referring now to FIG. 7, each lock 46 itself contains the lock board 140 as described above having a microprocessor 142 that is in communication with the control board 66 of its respective module 12 such that the lock 46 can receive various instructions from the control board 66. These instructions can include unlock the lock or illuminate the LED lights, and the lock board 140 can pass back information to the control board 66 from its sensors, such as whether the lock is locked/unlocked, door is open/closed, a package is within locker, temperature, and the like. Power to the locks 46 can also be supplied through the respective control boards 66.

As discussed with respect to FIGS. 2B-2E, the lock board 140 includes the microprocessor 142 and the two ports 144*a*, 144*b* for communication with the control board 66 and further locks 46. The lock boards 140 are arranged in daisy chain fashion such that each lock 46 has an input port 144*a* and an output port 144*b*. When the control board 66 provides an unlock instruction, for example, the instruction will travel from the control board 66 to the input 144*a* of the lock board 140 and then to the microprocessor 142 of the lock board 140 and to the lock board output 144*b*. The instruction will then pass from the output 144*b* to the input of the next lock board 140 in the module, and the process will be repeated. Each lock board 140 will determine if the instruction is directed to it, and, if so execute the instruction. Otherwise, it will ignore the instruction.

The lock board 140 further includes an output 146 for the LED light 48 and an output to a solenoid driver 148, which can drive the actuator 150 within the lock 46, thereby locking and/or unlocking the lock 46 on the door 40 to the locker 18 as described above. Again, other forms of locks and electronic lock control may be used. The lock board 140 can also receive an input from the switch 152 that informs the lock board of the position of the lock 46 and direct that signal to the control board 66. Because each lock 46 includes its own microprocessor and memory, the system 10 is flexible and actions taken with respect to the lockers 18 can be controlled at the lock board 140 rather than at the control board 66. For example, the lighting can be controlled by logic stored on the lock board 140 itself, rather than signals direct from the control board 66.

Referring now to FIGS. 8A, 8B, 8C, and 8D, each locker 18 of the modules 14, 16 may include a door damper 200 to control the response of a locker door 40 as the door 40 is opened and closed. Each locker 18 includes a frame 210 that defines the opening for the interior 42. The frame 210 includes a lower cross member 212, a first upright 214 on the hinge side, a second upright (not shown) opposite the first upright, and an upper cross member (not shown) opposite the lower cross member.

Disposed on the first upright 214 is the door damper 200. In this embodiment, the door damper 200 is a locker nub 200 that is disposed on the first upright 214 and extends outwardly relative to the interior 42 of the locker 40. The nub 200 includes a protruding head made of nylon, polytetrafluoroethene (PTFE), acetal resin, or another resilient, wear-resistant material. The nub 200 can take the form of a button-head pin with a shaft that is interference fit into a hole in the upright 214 or other button-type structures known to those of skill in the art. In this example, the nub 200 is manufactured from nylon 6.

Figure 8A:
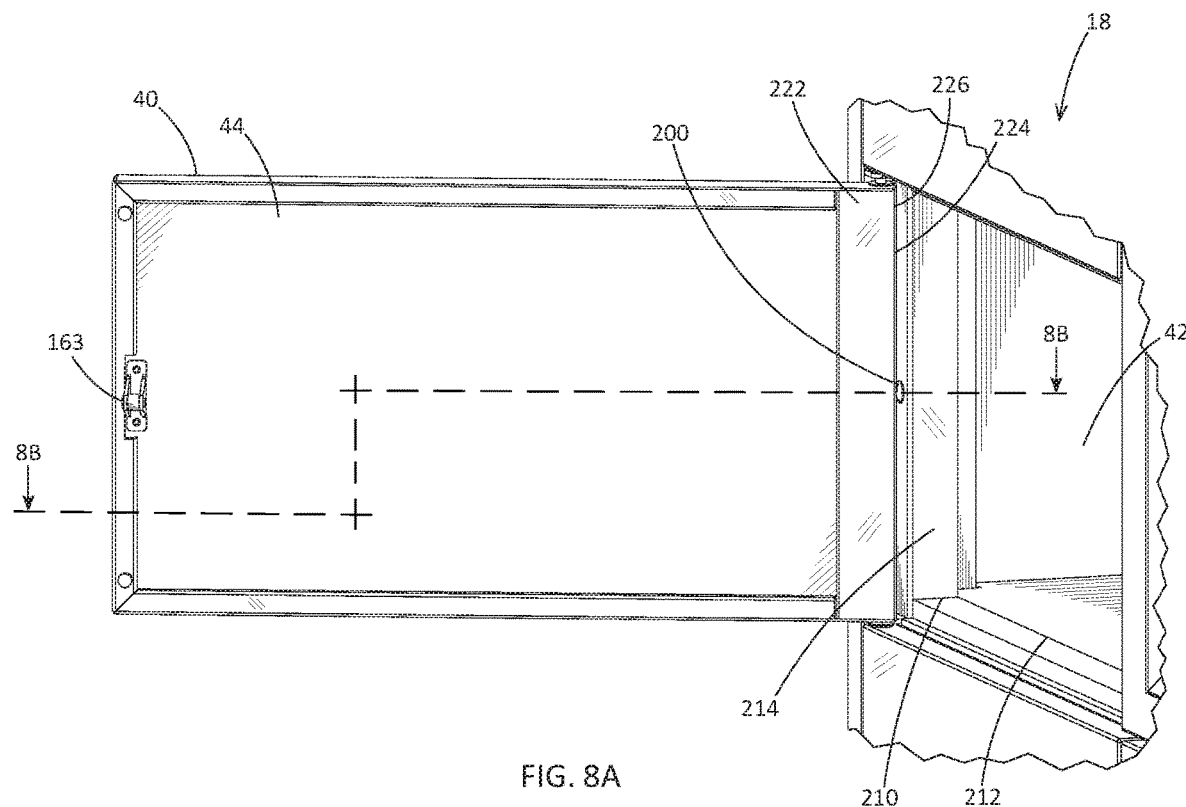
FIG. 8A is a detail perspective view of a locker of the package delivery system of FIG. 1 in a fully open position.
Figure 8B:
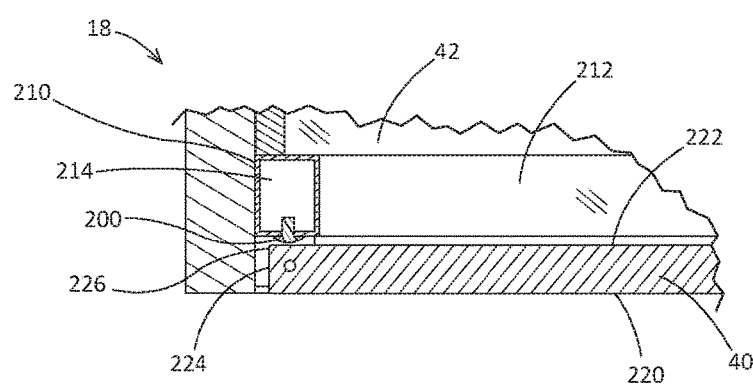
FIG. 8B is a simplified schematic sectional view of the locker of FIG. 8A in a closed position, taken along section line 8B-8B in FIG. 8A.

Each locker door 40 includes a front face 220, a rear face 222, and spine 224. The rear face 222 and the spine 224 meet at a rear edge 226. The locker nub 200 is disposed at a particular location on the first upright 214 of the locker 18 such that, when the locker door 40 is in a closed position as shown in FIG. 8B, the rear face 222 either does not touch the nub 200 or bears slightly against the nub 200. After the locker door 40 is unlocked, and thus begins to automatically swing open due either to the spring-biasing or the unlocking force of the lock 46, the nub 200 soon after either engages in frictional contact with the rear edge 226 or generates an increased level of frictional force by bearing further on the rear edge 226. This frictional force of the rear edge 226 bearing against the nub 200 is greater than the force of the door 40 opening and is therefore sufficient to slow the rotation of the door 40 until finally bringing the rotation to a halt at a partially open position as shown in FIG. 8C.

By controlling the opening response of locker door 40 in this particular manner, the locker door 40 is hindered from fully opening automatically upon unlocking and may be helpful to prevent a locker from opening onto an unsuspecting person.

Figure 8C:
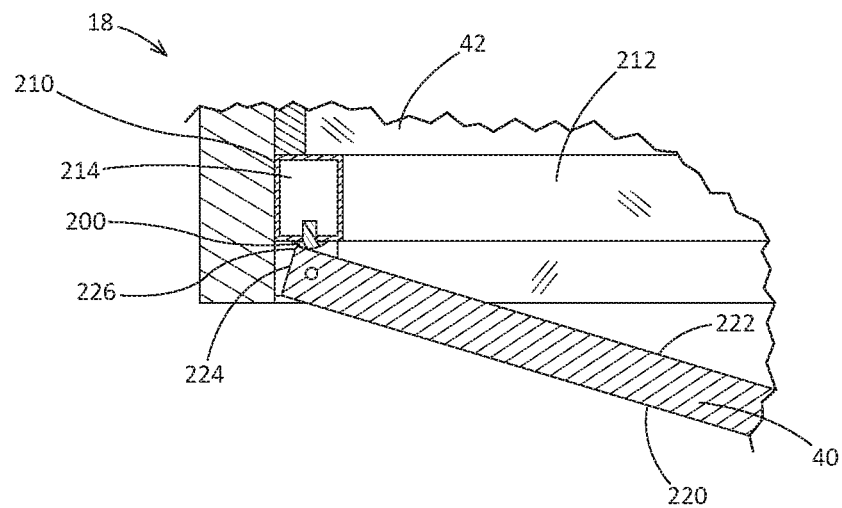
FIG. 8C is a simplified schematic sectional view of the locker of FIG. 8A in a partially open position, taken along section line 8B-8B in FIG. 8A.
Figure 8D:
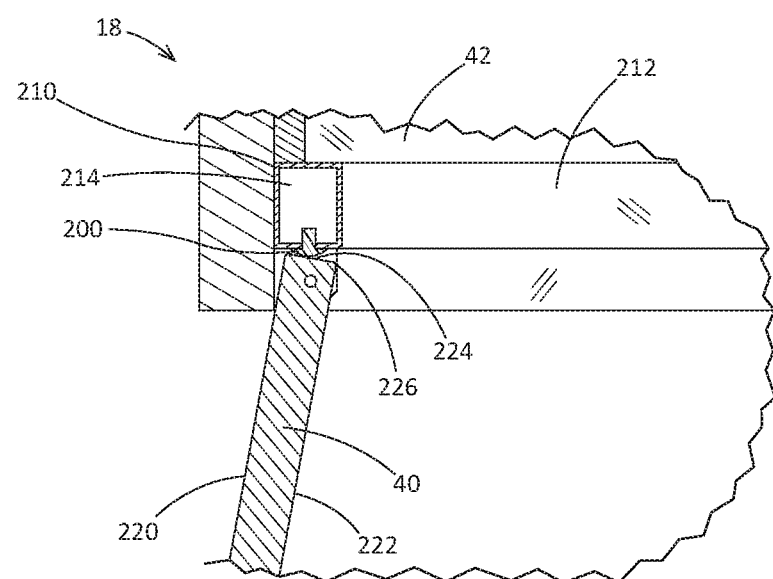
FIG. 8D is a simplified schematic sectional view of the locker of FIG. 8A in a fully open position, taken along section line 8B-8B in FIG. 8A.

With the locker door 40 now stably resting in the partially open position as shown in FIG. 8C, a user may thereafter manually open the door 40 further to a fully open position. As the user manually opens the door 40, the rear edge 226 continues to bear against the nub 200, thereby elastically deforming the nub 200. Further manual opening of the door 40 by the user overcomes the increased friction applied by locker nub 200, and the user places the door 40 in the fully open position as shown in FIG. 8D. As further shown in FIG. 8D, due to the particular location of locker nub 200, the nub 200 either disengages from frictional contact with the rear edge 226 or applies a decreased level of frictional force by only slightly bearing on the rear edge 226 when the door 40 is placed in the fully open position. The nub 200 maintains the locker door 40 in the fully open position shown in FIG. 8D because, if the locker door 40 begins to close again, the rear edge 226 of the locker door 40 may reengage frictional contact with locker nub 200. As such, once placed in the fully open position, locker 40 will thus be able to maintain the fully open position and resist being inadvertently closed due to weak external closing forces, such as light winds, accidental bumps, or gravity if the package delivery system 10 is at an angle.

With locker door 40 now stably resting in the fully open position as shown in FIG. 8D, the user may more easily access the locker interior 42, allowing items to be deposited and retrieved from inside the locker 18. Once the user is done using the locker 18, she may thereafter manually close the door 40, overcoming the friction applied by locker nub 200, and placing the door 40 in the closed position as shown in FIG. 8B.

The manner of control of locker door 40 by locker nub 200 when the door 40 is not locked may be characterized as behaving similarly to a bi-stable system, where the locker door 40 is substantially at rest when in either the partially open position as shown in FIG. 8C or the fully open position as shown in FIG. 8D, and where the locker door 40 resists being placed in an intermediary position between the two resting positions due to the frictional contact of locker nub 200. Other bi-stable systems, such as spring-loaded systems and magnetic systems, and other shapes for the nub, such as a ramp or a resilient lining of the surface of the upright 214, may be used.

Figure 9:
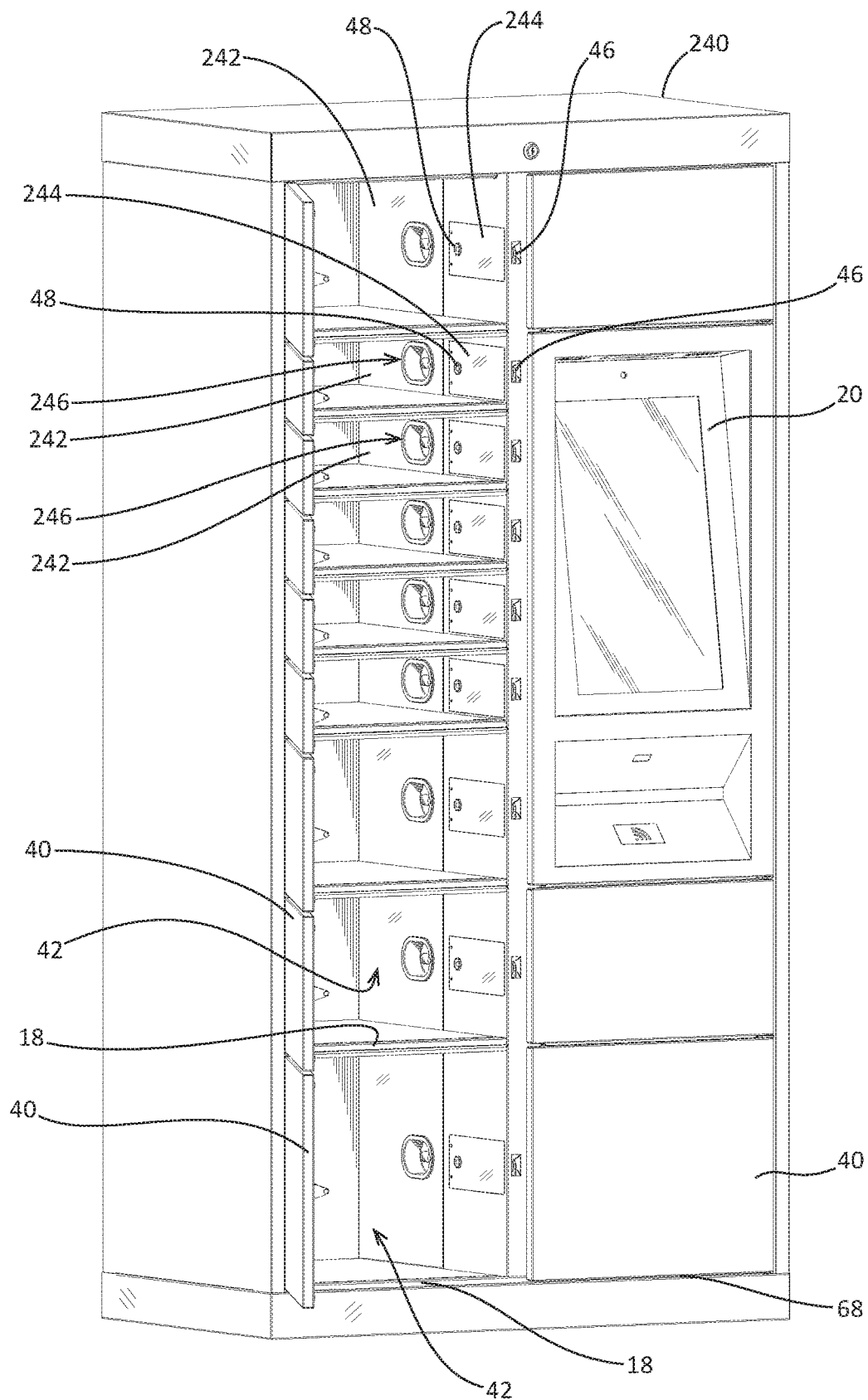
FIG. 9 is a perspective view of a second embodiment of a control module of the package delivery system of FIG. 1 with a plurality of locker doors in a fully open position, where each locker interior includes a sterilizing lamp.
Figure 10:
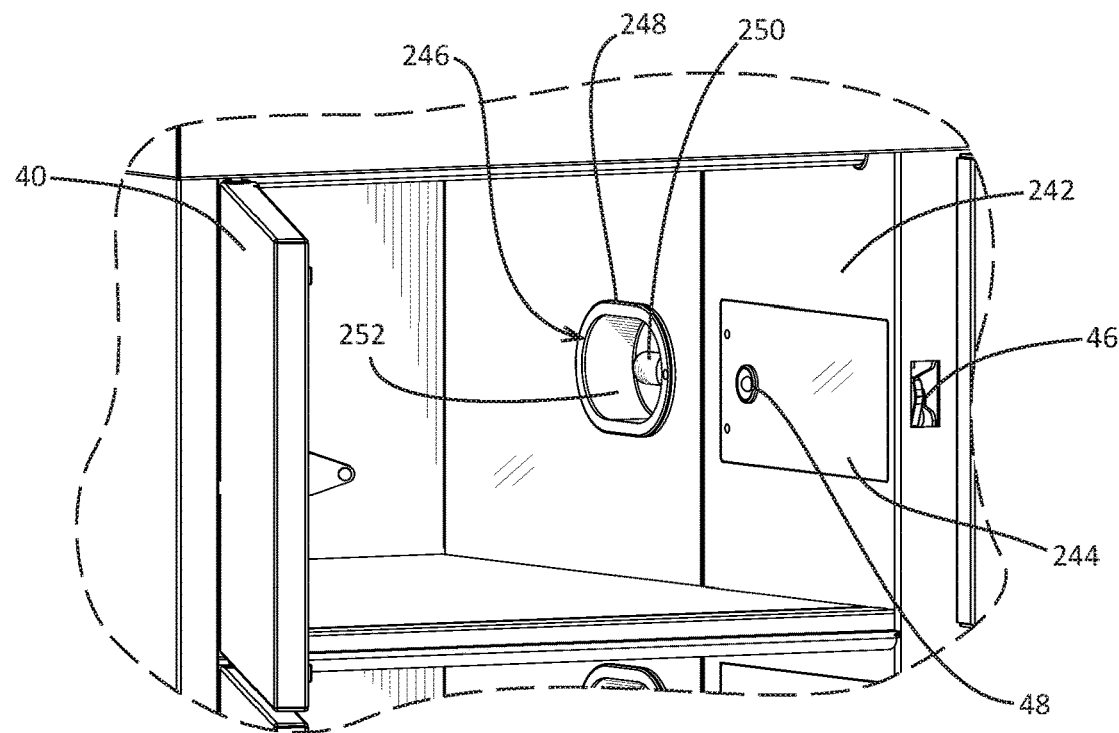
FIG. 10 is a perspective view in partial breakaway of an interior panel and the sterilizing lamp of the control module of FIG. 9.
Figure 11:
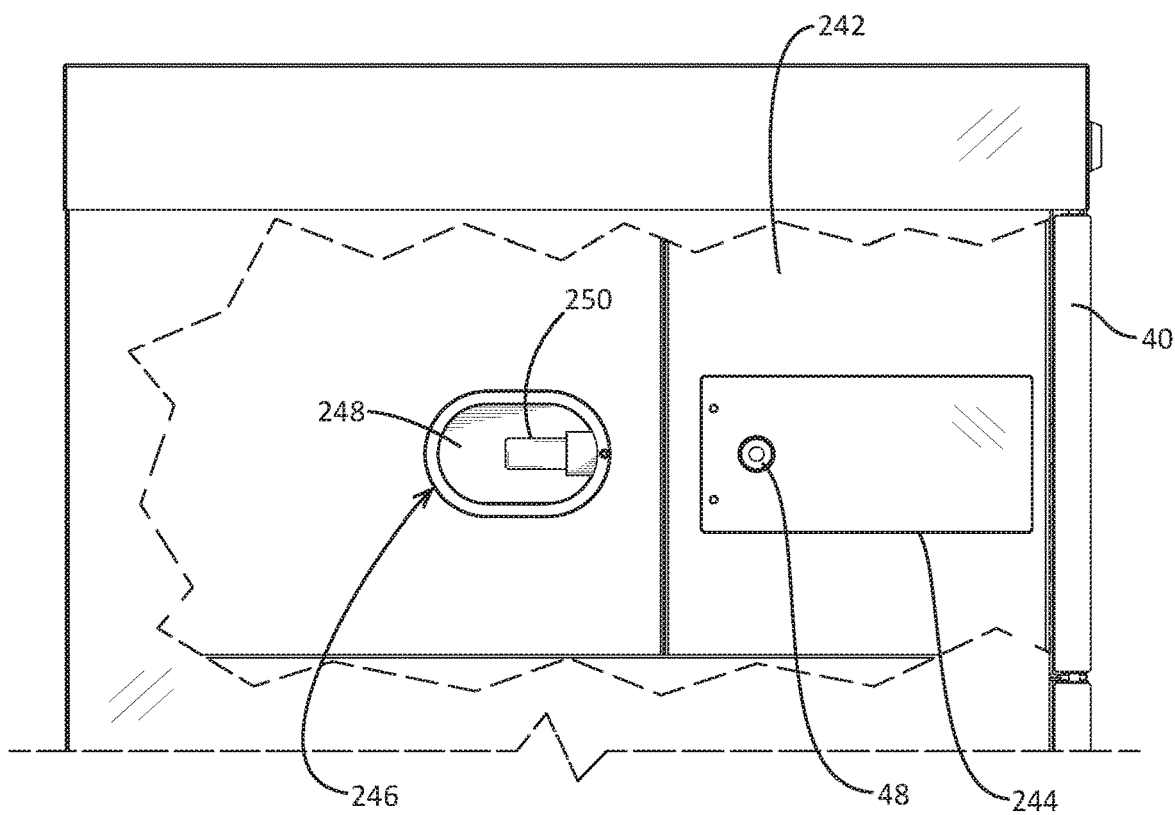
FIG. 11 is a plan view in partial breakaway of the interior panel and sterilizing lamp of FIG. 10.

Referring now to FIGS. 9-11, a second example of a control module 240 is depicted. In this example, the control module 240 is constructed generally similarly to the control module 14, with a series of lockers 18, each having a locker door 40 and a locker interior 42. In this example, the locker doors 40 are solid, but they could have windows 44 as in previous examples.

The lockers 18 further include locks 46 and lights 48 as in previous examples, and as better seen in FIGS. 9 and 10, each locker 18 includes an interior side 242 on which is disposed a removable lock panel 244. In these examples, the lights 48 are disposed in the removable lock panels 244 and are connected as described above to the lock boards 140. The lock panels 244 can be removed to gain access to the locks 46 for troubleshooting, updating, and replacement when necessary.

In this example, each locker 18 can further include a UV lamp 246, each UV lamp 246 having a transparent cover 248 that allows passage of UV light, a UV light 250, and a reflective housing 252. Each UV lamp 246 is also in electrical connection with its respective lock board 140, thereby receiving both power and control from the lock board 140.

In this example, the UV lamp 246 emits UV-C light waves and is a sterilizing lamp. This form of lamp is useful for destroying the ability of bacteria, viruses, and other pathogens to reproduce. In other words, the UV lamp 246 may be used to help remove pathogens from the surface of a package stored in the unit, and it may thereby improve the safety of the system for the package recipients. UV light in this spectrum may also be harmful to humans, and care must be taken in designing the unit to prevent humans from contacting the UV light. For example, the lockers 18 may be designed such that the locker doors 40 will not open while the UV lamp is illuminated. Moreover, if the locker door 40 is open, the UV lamp 246 is unable to illuminate. The UV lamps 246 can be connected to the lock board 140 in known manner, and each microprocessor 142 of the lock board 140 can control operation of the respective UV lamp 246 in connection with the operation of the lockers 18, locker doors 40, and locks 46.

In one process, the courier places a package in an empty locker 18 and closes the respective locker door 40, which can inform the lock board 140 that a package has been placed in that locker 18. The lock board 140 then causes the illumination of the UV lamp 246 for a specified period of time effective to help eliminate pathogens from the surface of the package. During this period of time that the UV lamp is illuminated, the lock board 140 prevents the lock 46 from opening. Moreover, if the lock 46 is opened manually, or if the door 44 is force opened, each locker 18 can include sensors that inform the lock board 140, and the lock board 140 can immediately extinguish the UV lamp 246. Further, if windows 44 are to be used in the doors, the transparent material used for the windows 44 must be capable of blocking the UV light.

Figure 12:
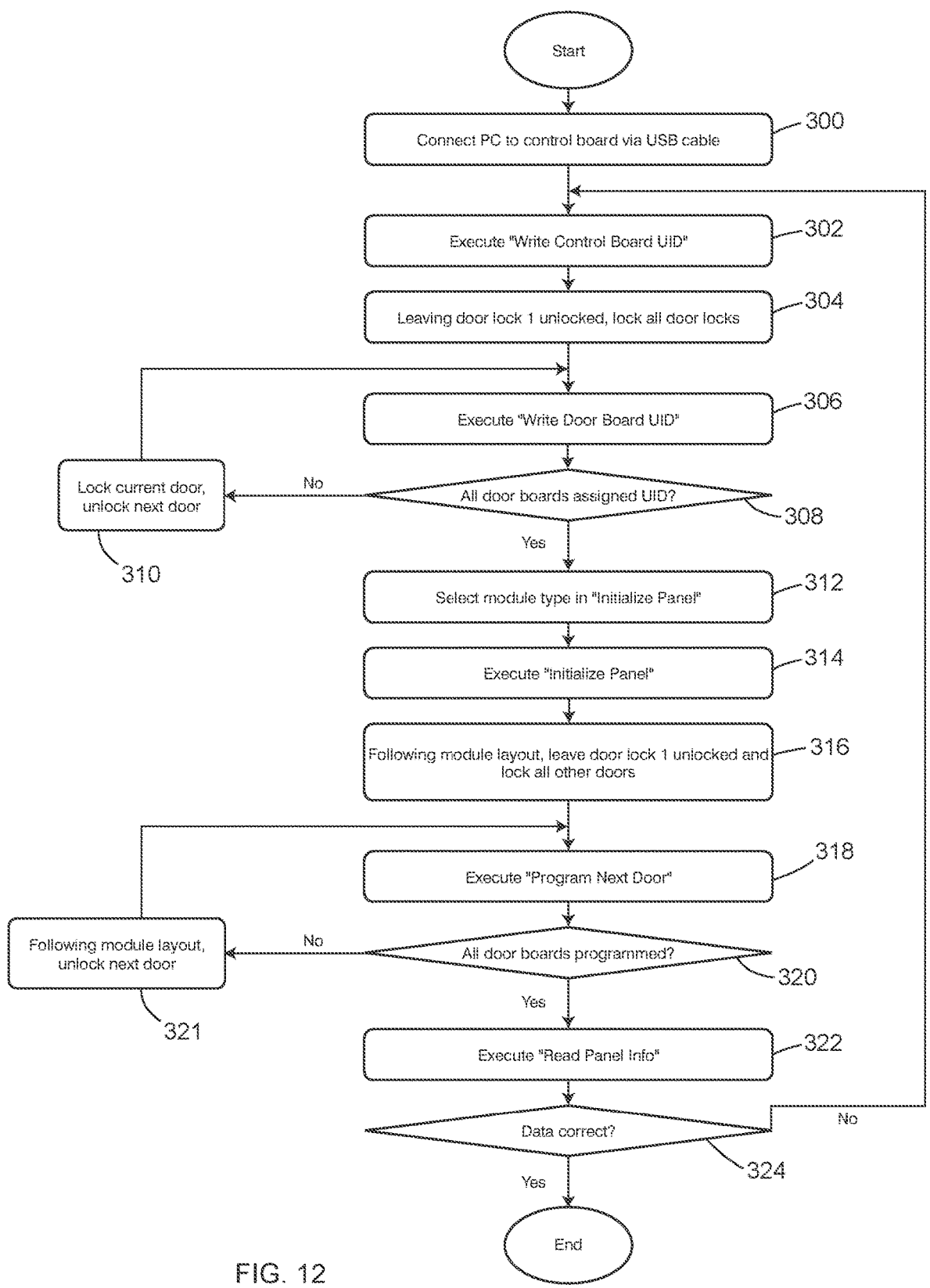
FIG. 12 is a flow chart describing an example of an initialization procedure for the locks in the package delivery system of FIG. 1.

Referring now to FIG. 12, prior to use, the control boards 66 for each module 12 may be programmed and each lock 46, disposed in each locker 18, may be mapped to the package delivery system 10 such that the control system 60 knows which lock 46 is disposed relative to each locker 18. Referring to FIG. 12, a user such as a technician first connects his or her computer to the control board via the USB port 122 at step 300. The technician executes a program that initializes the control board 66 and provides it with a unique identification number ("UID") at step 302. That UID will be used by the main board 62 for address purposes.

The technician may then provide a unique identification number to each of the locks 46 in the module 12. The technician may start by unlocking all of the locker doors 40, such as by using the kiosk 20 as described above or by operating the mechanical override lock 51 by use of a corresponding key. With all locker doors 40 open, the technician manually places the lock 46 in the upper-most position in the left column 28 in the unlocked position, such as by leaving the corresponding locker door 40 open. The technician then manually places all remaining locks 46 in the locked position at step 304, such as by closing the corresponding locker doors 40 in the closed position. The technician executes a program on his or her computer that generates a UID and assigns it to the lock 46 in the unlocked position in step 306. The technician reviews whether all locks 46 have been assigned UIDs at step 308, and, if not, the technician then manually places that lock 46 in the locked position, then places the lock 46 in the locker 18 immediately below the first locker in the unlocked position at step 310. The technician then executes the same program at step 306, which assigns a second randomly generated UID to the second lock. The technician continues in this manner reaching the bottom locker of the left column 28, then moving on to the top locker 18 in the right column 30, then moving down until reaching the bottom locker 18 in the right column 30 until all locks 46 have been assigned UIDs. In this way, each microprocessor 142 in each lock board 140 is provided with a unique identification number.

The technician may then map each lock 46 to its position within in the module 12. The technician calls a mapping program, here called "Initialize Panel," at step 312, and within that program identifies which configuration of module 12 is being used. In most embodiments, there will be a few pre-programmed configurations of modules 12 having varying locker layouts and sizes. In this disclosure there are three configurations—the control modules 14, the first associate module 38, and the second associate module 39. By selecting from the pre-programmed configurations, the control board 66 is instructed as to how many lockers 18 are present in each column 28, 30 and what the sizes of each locker 18 are. After selecting the configuration of module 12, the technician executes the program at step 314.

The technician then, again, places the lock 46 in the upper left locker in the unlocked position, and all other locks are placed in the locked position at step 316. The technician then executes a third program, here called, "Program Next Door," at step 318 which maps the unlocked lock 46 to the location of the locker 18 within the module 12. The technician then reviews whether all locks 46 have been mapped at step 320, and then unlocks the lock 46 directly beneath the first lock at step 321, and then executes Program Next Door again at step 318. The technician continues in this way, first moving downwardly to the locker 18 at the bottom of the first column 28, then to the locker 18 at the top of the right column 30, then down again to the locker 18 at the bottom of the right column 30. After all locks 46 are mapped, the technician can execute a final program at step 322 that will output the locker locations and the lock UIDs for review. Here, that program is called, "Read Panel Info." The technician reviews the output at step 324 to ensure that he or she has mapped all locks 46 correctly. If there is incorrect mapping, the technician can start again at step 302. Of course, the titles of the programs are for description only and no limitations should be read therefrom.

Other mapping protocol could be used. For example, instead of identifying which of the locks 46 is unlocked to assign the lock UID, the program used by the technician may instead identify which of the locks 46 is locked to assign the lock UID. For example, the system could again start with all locks unlocked and all locker doors open. The technician can then close the upper left locker door, then execute "Program Next Door." The user would then close the locker door immediately below the first and execute Program Next Door. The user would continue with the remaining doors as described above.

Figure 13:
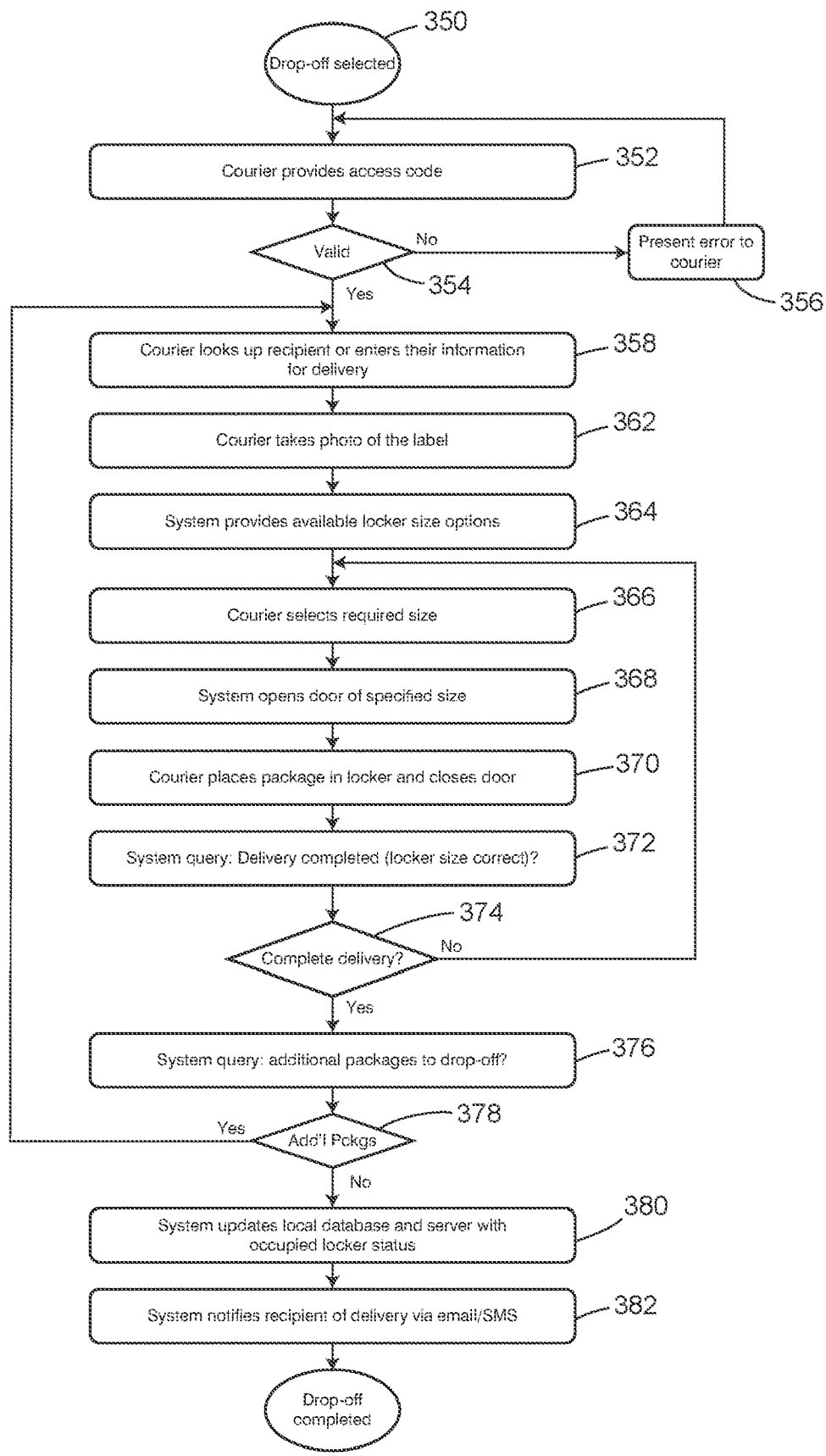
FIG. 13 is a flow chart describing a first example of a drop-off process for storing an item in the package delivery system of FIG. 1.

Referring now to FIG. 13, a first example of a delivery procedure will be discussed. A courier, who has previously been registered with the system, approaches the package delivery system 10 and the touchscreen 22 displays at least two exemplary options: "PICK-UP" and "DROP OFF." In step 350, the courier selects the options "DROP OFF" by touching the touchscreen. After selecting drop-off, the courier is prompted to enter his or her access code or other credentials at step 352. The access code can be a numeric sequence such as a PIN code, an RFID tag, NFC, a Bluetooth signal, a BLE signal, or any other known system of authentication. The package delivery system 10 then analyzes the access code at step 354, and if the access code is not valid, it presents an error code at step 256 and returns to step 352.

If the access code is valid, the courier is prompted by the touchscreen 22 at step 358 to enter the recipients' name, email address, or other identifying information. Using the touchscreen, the courier enters a portion of the recipient's name or other information, at which time the package delivery system 10 locates the recipient's name and associated email address. At step 362, the package delivery system 10 prompts the courier to take a photo of the package using the digital camera 92 of the kiosk 20 as proof that the package was delivered.

After the digital photo is successfully captured, the system 10 prompts the courier at step 364 to select which size of locker 18 is needed to store the package. In the disclosed example, the touchscreen 22 provides icons of small, medium, and large, and the courier touches the screen icon at step 366 representing the size of locker 18 needed. The system 10 selects a locker 18 of the requisite type, informs the courier which locker 18 has been selected, and, at step 368, automatically unlocks the lock 46 of the selected locker 18 and the door 40 opens. The LED light 48 may illuminate at this point, with either steady illumination or flashing illumination. The courier then places the package in the locker 46 at step 370 and closes the door 40, with the lock 46 locking automatically after the door 40 is closed.

At step 372, the system 10 prompts the courier with a query of whether the courier completed the drop-off. At step 374, the courier responds, and if not completed, the system 10 returns to step 366 and prompts the courier to enter the size of the locker 46 needed.

If the drop-off was competed, the package delivery system 10 prompts the courier with an inquiry of whether any further packages are to be stored for other recipients at step 376. Again, the courier responds at step 378, and if further packages are to be delivered, the system 10 returns to step 358. If not, step 380 is performed, and the system 10 updates its local database on the main board 62 and the cloud-based server 80 with the occupied locker status. The status can include the locker UID, the time and date of delivery, and identification of package and recipient. The cloud-based server 80 will then update the database on any other control module 14 within the package delivery system 10. The cloud-based server 80 will then notify the recipient that his or her package has been delivered at step 382. In another example, the server 80 will update the local databases after completing the delivery and prior to step 376.

In certain instances, the recipient will not have registered with the system 10. If this happens, either the main board 62 or the server 80 will inform the administrator 82, and the administrator can inform the recipient that the package is waiting in a particular locker 18.

Figure 14:
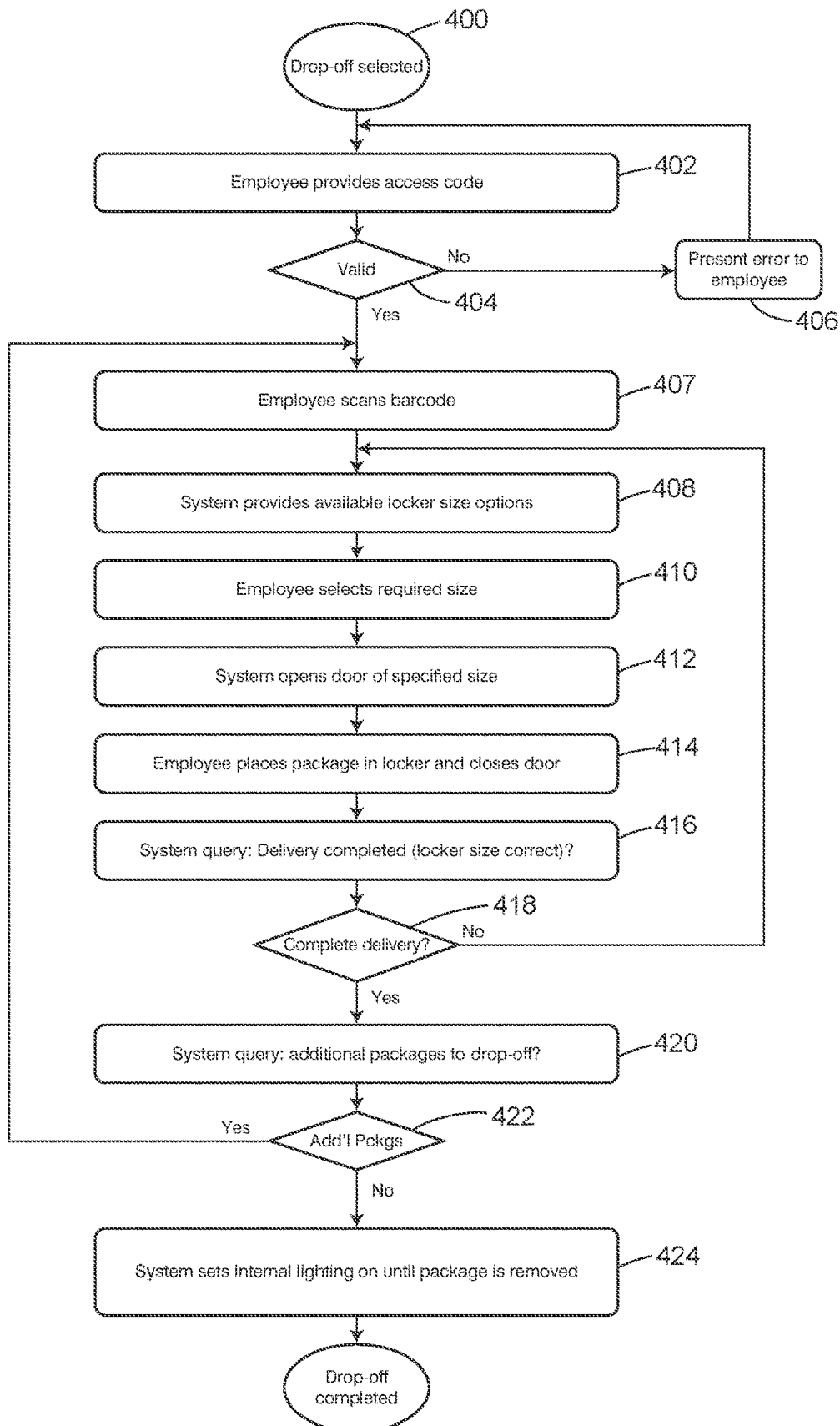
FIG. 14 is a flow chart describing a second example of a drop-off process for storing an item in the package delivery system of FIG. 1.

Referring now to FIG. 14, a second drop-off process is disclosed. The following drop-off process may be suitable for a retailer that accepts orders through its website or other on-line system, and then fulfills the order by locating the item within its retail environment (or by having the item shipped to the retail store) and storing it in a locker 18 within the store to await pick-up by the customer. Thus, after an order is placed and the employee has located the item, the employee approaches the delivery system 10. The touchscreen 22 prompts the employee with the choices of drop-off or pickup, and in step 400, the employee selects drop-off. The employee next inputs his or her access code at step 402. Again, the access code can be a numeric code, RFID, Bluetooth, or any other known authentication process or procedure. The main board 62 determines whether the access code is valid at step 404, and if not, the touchscreen 22 provides an error message at step 406 to the employee and returns the system 10 to step 402 to request a valid access code. If the access code is valid, the package delivery system 10 prompts the employee to scan the barcode associated with the order with the barcode reader 24. In other words, it is understood that retailer will generate an access code such as a barcode and associate that barcode with the order. Of course, other access codes, such as numeric codes, can be used.

After the employee scans the barcode at step 407, the touchscreen 22 prompts the employee with available size lockers at step 408, and the employee selects the required locker size at step 410 via the touchscreen 22. Much as in the previous example, the package delivery system 10 then indicates via the touchscreen 22 the locker 46 that will be used, and, at step 412, the system 10 unlocks the lock 46 associated with the locker 18, and the locker door 40 opens automatically due to being biased in the open orientation. At step 414, the employee places the item associated with the order in the locker 18 and closes the locker door 40. The system 10 then prompts the employee at step 416 with a query of whether the delivery for this particular order is complete. If the employee touches "no" at step 418, the system 10 returns to step 408 and queries the employee of which size locker 18 is necessary. If yes, the system 10 prompts the employee at step 420 regarding whether any additional orders are ready to be fulfilled. If the employee responds with "yes" at step 422, the system 10 returns to step 407 and requests the employee to enter the barcode associated with the next order. If the employee responds with "no," the system 10 directs the LED light 48 associated with the locker used by the employee to illuminate the locker 18 at step 424 until the package is removed.

The system 10 next informs the retailer's IT system via either its main board 62 or its cloud-based server 80 that the package associated with the order has been stored in a particular locker 46. It is understood that the retailer's IT system can then inform the recipient that the package is waiting for them in the selected locker 46. In this manner, the package delivery system 10 never possesses any information related to the recipient. The cloud-based server 80 can then update the databases of any other control modules 14 within the package delivery system 10 as described earlier. Again, the server 80 may update the local databases after the delivery is completed and before step 420.

Figure 15:
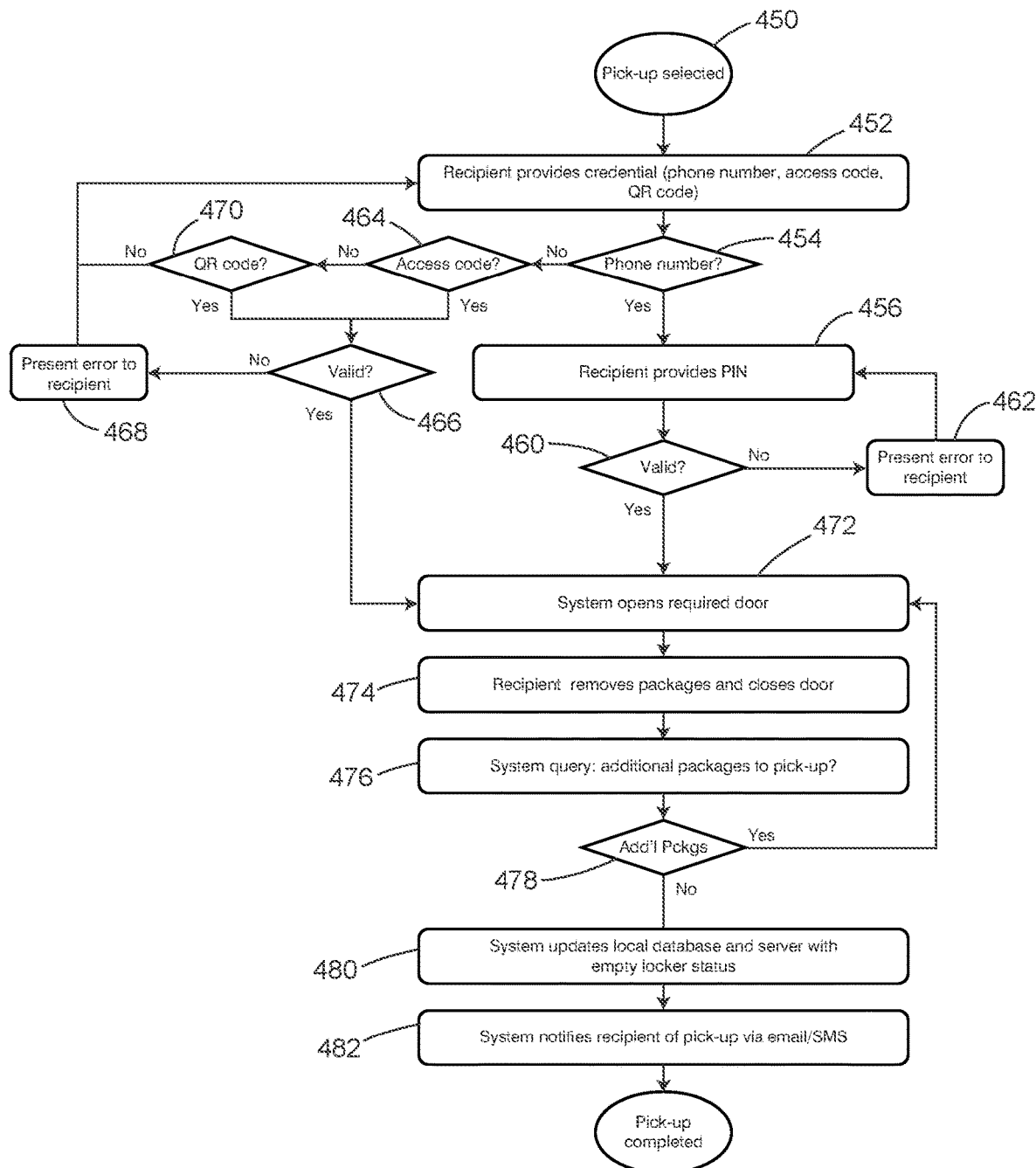
FIG. 15 is a flow chart describing an example of a first process for a recipient retrieving an item from the package delivery system of FIG. 1.

Referring now to FIG. 15, a first example of a pick-up process is disclosed, most useful with the drop-off process of FIG. 13. It is understood that the recipient has been notified via email that the package has been delivered and is awaiting at the package delivery system 10. The recipient may have already created an account with the system providing a telephone number and PIN code. Further, the email received by the user may provide an access code or a QR code.

In step 450, the recipient is provided with the same opening selection possibility as in the previous processes, i.e., "PICK-UP" or "DROP OFF," and the recipient selects "pick-up" on the touchscreen 22 of the kiosk 20. The touchscreen 22 then prompts the recipient for a credential at step 452 which can be the recipient's phone number, an access code provided in the email or a QR code provided in the email. After the credential is entered, the system 10 determines whether the recipient has entered a telephone number at step 454. If the recipient has entered a telephone number, the system then requests that the recipient provide his or her PIN code at step 456. After receipt of the PIN code, the system 10 will then determine if the combination of the telephone number and PIN code is valid at step 460. If not, the system presents an error message to the user at step 462 and returns to step 456 requesting a valid PIN code.

If the user did not enter a telephone number, the system determines whether the recipient has entered an access code provided in the email at step 464. If yes, the system 10 then determines if the access code is valid in step 466. If not valid, the system 10 presents an error message at step 468 and returns the system 10 to step 452. If the recipient did not present either a telephone number or an access code, the system next determines if the recipient input a QR code at step 470. If not, the system 10 returns to step 452 and await the user input of credentials. If the user did input a QR code via the barcode reader 24, the system 10 then determines if the QR code is valid at step 466. Again, if the QR code is not valid, the system 10 presents the user with an error message at step 468, then returns the system to step 452. In another example, the user can simply be provided the option of scanning the QR code at step 400, on the screen of the kiosk 20 at the same time as the option of drop-off or pick-up. After the recipient enters his or her credentials and the package delivery system 10 validates those credentials, the digital camera 92 can take a photo of the recipient for security reasons.

If any of the telephone number/PIN code, access code, or QR code is valid, the system 10 opens the associated locker door 40 at step 472. The recipient can remove the package and close the locker door 40 at step 474. The system 10 then prompts the recipient whether he or she is done picking up packages from this order at step 476. The recipient responds in step 478, and if not done, the system will return to step 472 and open the next locker door 40 associated with the order. If done, the system 10 updates the local database and the cloud-based server regarding the empty locker status at step 480. The system 10 can then further email or text message the recipient to notify them of the successful pick-up at step 482, and within that email or text message, the system 10 can include the photo taken of the recipient after the credentials were validated. As mentioned earlier, the cloud-based server 80 can perform the communication and update the other control modules 14 within the system.

Figure 16:
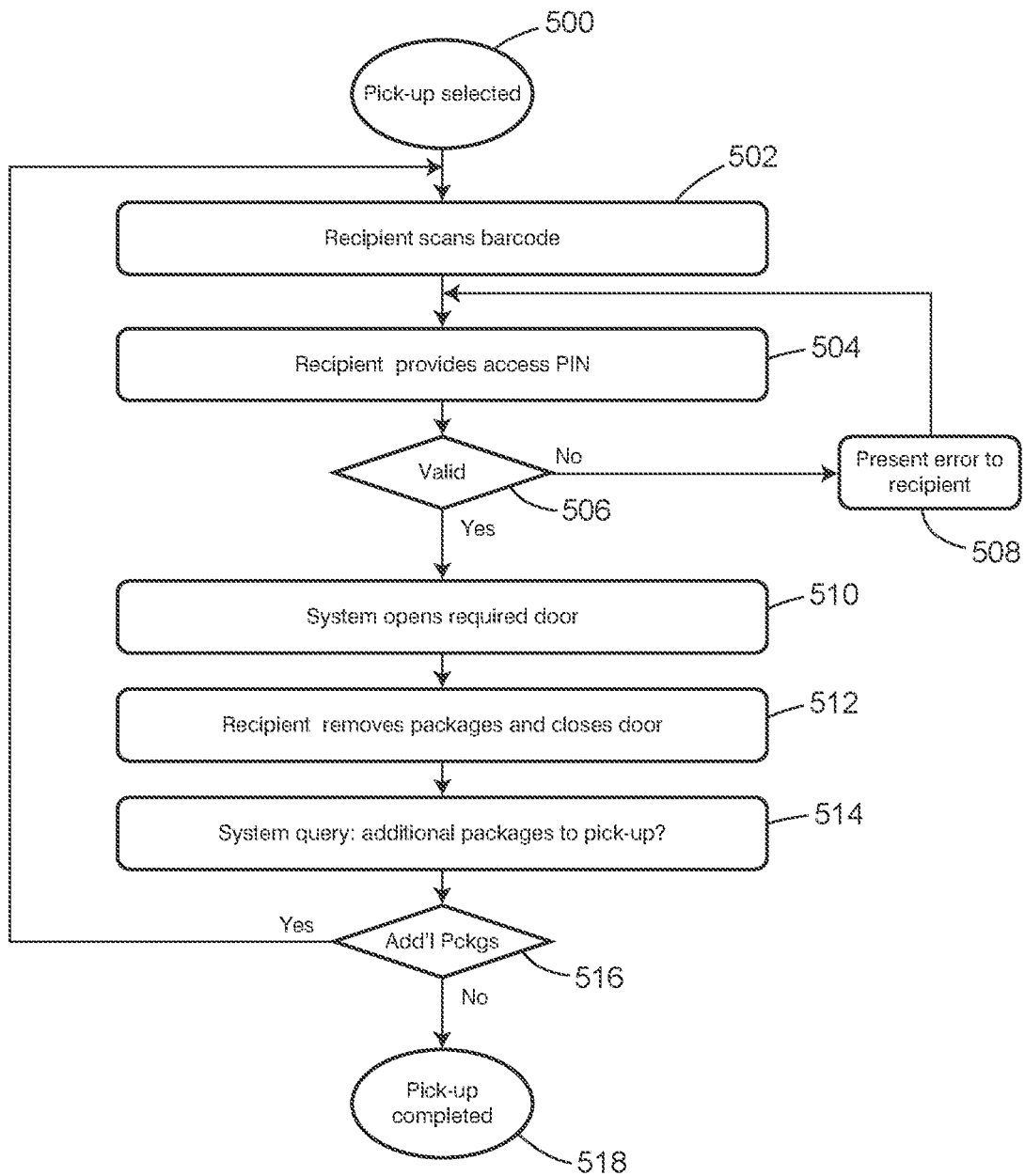
FIG. 16 is a flow chart describing a second example of a process for a recipient retrieving an item from the package delivery system of FIG. 1.

Finally, referring now to FIG. 16, a pick-up process that can be used in conjunction with the drop-off process of FIG. 14 is disclosed. Again, the recipient approaches the package delivery system 10 and selects pick-up in step 500. The recipient scans his or her barcode received in the email or text notification that the package was ready for pick-up at step 502. Next, the recipient enters his or her PIN code associated with his or her account at step 504. The system 10 evaluates the barcode and PIN code at step 506, and if not valid, presents an error message at step 508 and returns the system 10 to step 504 for re-entry of the PIN code. If the combination is valid, the system 10 opens the appropriate locker door at step 510. The recipient can then retrieve his or her item from the locker 18 and close the door 40 at step 512. The system 10 queries whether the recipient has additional packages to pick-up at step 514. If the recipient enters yes at step 516, the system returns to step 502 to allow the recipient to enter another barcode. If the user inputs "no," the system 10 moves to step 518 and updates the local database and the cloud-based server 80 and notifies the retailer's IT system that the package was picked up. The retailer, who again has information relating to the recipient, can email or text the customer to inform them that they package was retrieved.

Other functions can be added. For example, it is desirable that the recipient retrieves his or her package soon after it is delivered to the package delivery system 10. With rapid turnover, the couriers and the retailers can deliver more items. Accordingly, administrators may place a time limit on the amount of time that a package may be stored before being automatically returned. Certain couriers or retailers may seek to limit the time to three or four days. To address any issues with the recipient being unavailable during that time frame, the package delivery system 10 may include a vacation hold feature, whereby the recipient, upon receiving the notification that his or her package has been delivered, can request an extended time period with which to pick up the package. Thus, the system may default to a short three-day period, but the recipient can extend the time period to one week or more. The length of the vacation hold can be set by the administrator via an application or website running on the personal computing device 82.

In other features, the kiosk 20 can allow an administrator to access administration features directly on the control module 14. After logging in with an access code and PIN number, the administrator can select an "add module" function, and control module 14 will query whether another module 12 has been connected as described above. If so, the main panel 62 will execute a function recognizing the second module and enabling communications and control data to be sent between the two.

The display 22 can then display the names and locations of lockers 18 of the newly recognized module 12 and further can display touchscreen icons that allow a function to be called to open each door 40. In this way, the technician can ensure that the main board 62 of the control module 14 can control the lock boards 140 within the newly recognized module 12.

In another function, when an administrator logs in, the package delivery system 10 may provide the administrator a report of the packages that have been stored within the package delivery system 10 for too long. The administrator may then either set those packages for return to sender or return the items back to the sales floor.

The display 22 can further open a maintenance screen for servicing the package delivery system 10. The display can include touchscreen icons for ordering an entirely new module, for ordering a replacement control board 66, or for ordering replacement lock boards 140 for any of the locks 46 of the associated module 12. By touching the icon on the display, the main board 62 signals the cloud-based server 80, and the cloud-based server 80 can be configured to signal, for example, a service company, the manufacturer of the module 12, or a supplier of the parts.

Figure 17:
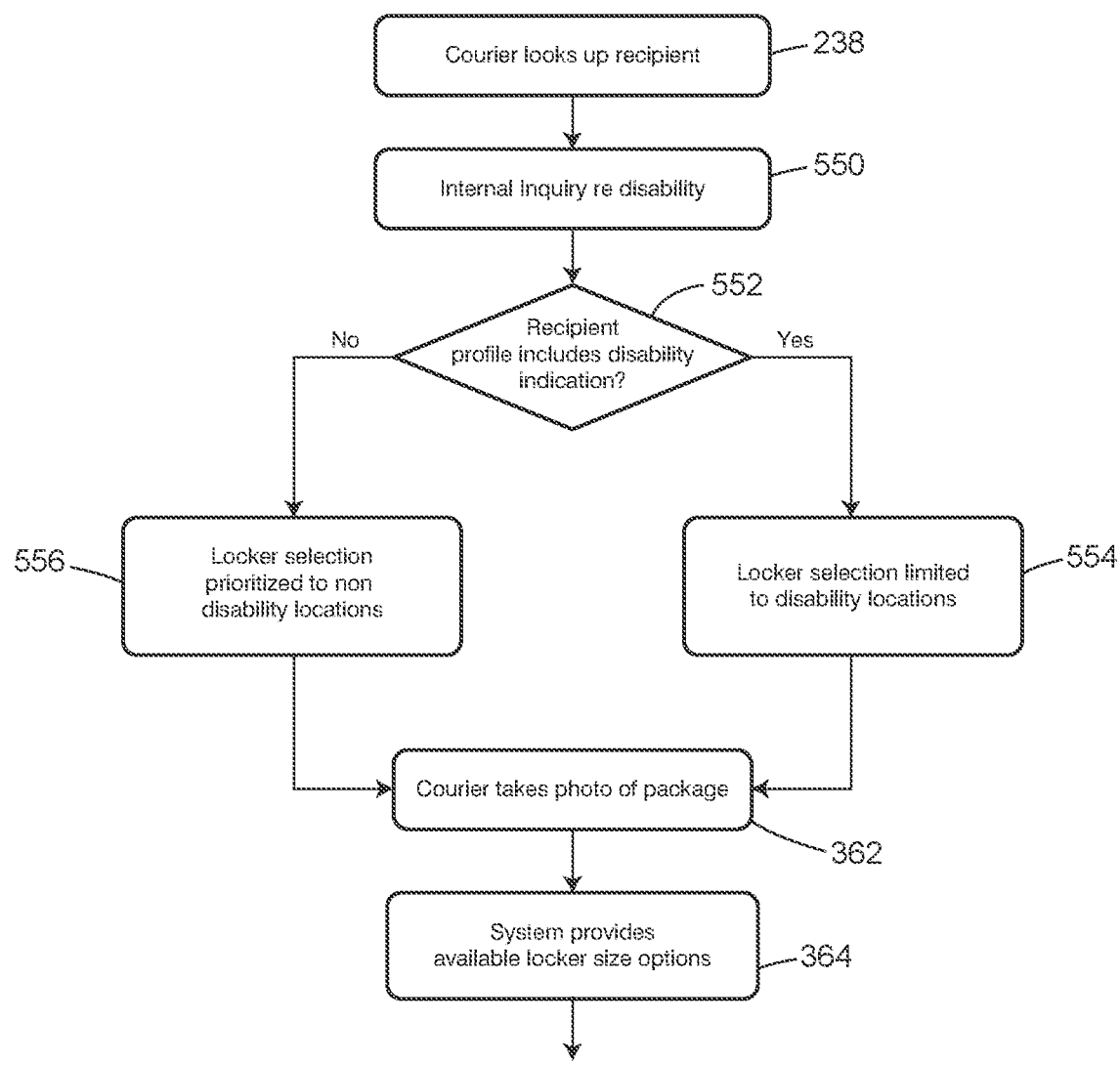
FIG. 17 is a flow chart describing a subroutine within the drop-off process for optimizing locker availability for the disabled.

Referring now to FIG. 17, the package delivery system 10 can be configured to allocate lockers in a way that optimizes locker availability for the disabled. FIG. 17 is a flowchart that is a subroutine that may be incorporated into the drop-off procedure of FIG. 13. One of ordinary skill will understand that it can be incorporated into the drop-off procedure of FIG. 14 as well. Accordingly, as disclosed with respect to FIG. 13, the courier in a drop-off procedure can, at step 358, look up the recipient by entering his or her name, email address, or other identifying information in the kiosk 20. Once the package delivery system 10 locates the individual, it can then review the individual's account to determine if that individual has a "disabled" indicator contained therein. In other words, when creating an account for the package delivery system, the recipient may check a box or otherwise indicate his or her status with regard to physical disability.

The package delivery system 10 can be programmed with an algorithm that optimizes locker selection for accessibility for the disabled. The package delivery system may have categorized the lockers into two groups: a first group that are highest off the ground and a second group that are lower to the ground and accessible to the disabled. The package delivery system will prioritize filling the lockers 18 that are highest off the ground for those recipients who are not disabled, and it will delay filling lockers 18 that are nearer the ground in an effort to save those lockers 18 for the disabled. Accordingly, the package delivery system 10 will review the account of the recipient of the package at step 552. If the recipient does have a disability indicator in his or her account, at step 554 the package delivery system will only allow those lockers in the second group to be filled. But if the recipient does not have a disability indicator in his or her account, the package delivery system will prioritize filling those lockers in the first group at step 556. Thereafter, the package delivery system 10 will proceed as in FIG. 13, and the system 10 will require the courier to take a photo of the package (step 362), provide the available locker size options (step 364), the courier will select the required size (step 366), and the system 10 will open the door of a locker of the specified size (step 368), with the locker being selected by the system 10 under the direction of the algorithm of steps 550-556.

In another aspect of the package delivery system 10, an application can reside on a recipient's personal computing device such as a smart phone that can simplify and speed interactions with the package delivery system 10. For example, the system 10 can push notifications to the smart phone indicating that a package has been delivered and is awaiting pickup. The system can also push notifications that the package will be returned if not picked up within a certain amount of time, and later, that a package has been returned for failure to retrieve. The app can also control or provide credentials via Mobile ID. Accordingly, the app can generate a unique identification for a recipient, and that recipient can provide that identification via mobile ID through, for example, NFC, Bluetooth, or BLE. The app can receive a QR code from the system 10 and provide an image of the QR code for scanning at the system 10.

In another aspect, the system 10 may be used in a retail store environment to protect against theft. Theft from a retail store environment, both from customers and employees, has long been a problem for retailers. In particular, certain items are small and expensive, and therefore are more likely to be subject to theft. One solution has been to place these items on a retail floor under lock and key in a cabinet. Accordingly, when a customer seeks to purchase that item, he or she must first locate a store employee to open the cabinet. This can be frustrating for customers, as store employees may not be available when needed. Even when a store employee can be located, the employee may take the product and immediately require the customer to purchase the product. This may not be satisfactory, as the customer may have to immediately wait in line to purchase that product, and he or she may then wish to continue shopping and be required to conduct a second transaction upon leaving the store. Further, this system does nothing to protect against employee theft. In another unsatisfactory solution, those products are stored behind the check-out counter or service counter, and the customer cannot access the product without first waiting in line. It would be a great advantage if a retailer could store and display high-value items in an access-controlled cabinet that both protected against loss as well as made the items more easily available to customers.

In a first example of improving control and reducing theft, the system 10 is placed on the floor within a retail environment. A customer can input on the kiosk 20 an identification of the locker display case 18 (the display cases 18 may be individually numbered, for example) and, if applicable, the number of products desired. As noted above, the kiosk 20 can include a touchscreen display 22 and a camera 92. The customer can, by using the touchscreen display 22, indicate which display case 18 to open. The camera 92 will take a picture of the user, and the system 10 will store the photo, either at the kiosk 20 or on the server 80. The system 10 will then open the display case 18, allowing the user to retrieve the desired product. The user, knowing of the recording of the photograph and identification of the goods taken, will be less likely to commit theft of the goods.

Facial recognition technology and artificial intelligence can also be employed at the register and at the retail store exits to determine if the user has paid for the goods. The cloud server 82 can be connected to the retail store's security systems By using known techniques of comparing the photo of the user with video taken at the retail store registers and the exits, and further by cross-referencing the user's purchased goods against the goods identified at the kiosk, it can be determined whether the user paid for the goods while checking out. Moreover, the goods stored in the display cases 18 may include security devices affixed thereto or other identification devices. These devices can alert the cloud server 80 when the goods are purchased and/or removed from the store premises.

In a second example of protection against retail theft, the user can inform the administrator that he or she would like to retrieve a stored good. As noted above, the kiosk 20 can include a display 22, a camera 92, a microphone, and a speaker. Further, the kiosk 20 can be connected to a personal computing device 82 operated by the retail store administrator via the network 79 as described above. The main board 62 of the kiosk 20 can be programmed such that a customer can initiate a request at the kiosk 20, which will then alert the administrator. The customer can interact with the administrator and indicate the specific display case 18 that he or she would like opened to access the product contained therein. The customer can communicate the request using one or more of the touchscreen display 22, the microphone, and the camera 92. The camera 92 can take a photo of the customer, which can be saved either at the administrator's CPU 82 or on the server 80. The administrator can ask how many of the products the customer will be taking, and upon receiving a response, can then initiate an unlocking of the requested display case 18. The user, knowing that his or her photo is stored along with a record of the product retrieved, in combination with potential facial recognition technology at the register and exit as discussed above, will be far less likely to shoplift.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

The invention claimed is:

1. A locker system, comprising:
a module including a first locker and a second locker, the first locker including a first light, the second locker including a second light, each light configured to illuminate an interior of its respective locker;
a control board disposed in the module;
a first lock board associated with the first locker and a first lock;
a second lock board associated with the second locker and a second lock;
the first and second lock board each including a processor and memory, each lock board further including an input port for receiving control signals and a first output port for forwarding control signals, each lock board further including a second output port, wherein the second output port of the first lock board is coupled to the first light, and the second output port of the second lock board is coupled to the second light; and
wherein the control board is in communication with the input port of the first lock board, wherein the first output port of the first lock board is in communication with the input port of the second lock board;
wherein the control board is configured to transmit a lock instruction to the first lock board, wherein upon receipt of the lock instruction, the first lock board is configured to read the instruction and transmit the instruction to the second lock board.

2. The locker system of claim 1, wherein the first light is an LED.

3. The locker system of claim 2, the first locker further comprising an auxiliary light, the auxiliary light being a UV light.

4. The locker system of claim 1, wherein the first light is a UV light.

5. The locker system of claim 4, wherein the first lock board is configured to illuminate the UV light for a predetermined period of time upon insertion of a package within the first locker.

6. The locker system of claim 1, wherein the first lock board is configured to illuminate the first light while a package is disposed within the first locker.

7. The locker system of claim 1, the lock instruction further including a unique identification associated with the first locker or the second locker.

8. The locker system of claim 7, wherein the first lock board is configured to perform a lock function if the unique identification is associated with the first locker.

9. A locker system comprising:
a control module including a kiosk having one or more input devices, a main board having a processor in communication with the kiosk, and a first control board having a processor in communication with the main board, the first control board further including a first control output and a first lock output,
the control module further including a first locker, a first lock board and first lock associated with the first locker, the first lock board including a processor in communication with the first lock output;
an associate module having a second control board having a processor in communication with the first control output, the second control board further including a second control output and a second lock output; and
the associate module further including a second locker, a second lock board and a second lock associated with the second locker, the second lock board including a processor in communication with the second control board;
wherein the second control board is releasably connected to the first control output.

10. The locker system of claim 9, the second lock board including an input port and an output port, the input port in communication with the second lock output of the second control board.

11. The locker system of claim 10, the associate module further comprising a third locker, a third lock board and a third lock associated with the third locker, the third lock board including a processor and having an input port and an output port, the input port of the third lock board in communication with the output port of the second lock board.

12. The locker system of claim 9, wherein the main board further comprises connecting means for connecting to an external network.

13. The locker system of claim 12, wherein the connecting means is one or more of a wireless antenna and an ethernet port.

14. The locker system of claim 12, wherein the main board is configured to communicate status information with a remote server via the connecting means.

15. The locker system of claim 9, wherein the input device is one or more of a touch screen display, an RFID reader, a mobile ID reader, a barcode scanner, and a camera.

16. The locker system of claim 9, wherein the first lock board is configured to receive a lock instruction from the first control board.

17. The locker system of claim 16, wherein the first lock board is configured to transmit the lock instruction to the second lock board.

18. The locker system of claim 9, wherein the first lock board further comprises a lamp power outlet.

19. The locker system of claim 9, wherein the associate module is configured to be communicate with a second associate module or a second control module via the second control output of the second control board.

20. The locker system of claim 9, the associate module further comprising a third locker, a third lock board, and a third lock associated with the third locker, wherein the second locker is within a first column of lockers in the associate module, wherein the third locker is within a second column of lockers in the associate module.

* * * * *